(12) United States Patent
Rüsing et al.

(10) Patent No.: US 7,105,324 B2
(45) Date of Patent: Sep. 12, 2006

(54) **NUCLEIC ACID ISOLATED FROM *TETRAHYMENA* WHICH CODES FOR A TRITERPENOID CYCLASE, ITS PRODUCTION, AND USE**

(75) Inventors: Matthias Rüsing, Köln (DE); Thomas Schweins, Düsseldorf (DE); Petra Dresler, Kriftel (DE); Wolfgang Stock, Düsseldorf (DE); Thomas Kiy, Frankfurt am Main (DE)

(73) Assignee: Nutrinova Nutrition Specialities & Food Ingredients GmbH, Frankfurt am Main (DE)

( * ) Notice: Subject to any disclaimer, the term of this patent is extended or adjusted under 35 U.S.C. 154(b) by 416 days.

(21) Appl. No.: 10/457,452

(22) Filed: Jun. 10, 2003

(65) Prior Publication Data

US 2003/0207317 A1 Nov. 6, 2003

Related U.S. Application Data

(62) Division of application No. 09/725,735, filed on Nov. 30, 2000, now Pat. No. 6,645,751.

(30) Foreign Application Priority Data

Dec. 1, 1999 (DE) ................................ 199 57 889

(51) Int. Cl.
*C12P 7/64* (2006.01)
(52) U.S. Cl. ...................................... 435/134; 536/23.2
(58) Field of Classification Search ................ 435/134; 536/23.2

See application file for complete search history.

(56) References Cited

U.S. PATENT DOCUMENTS 5,744,301 A 4/1998 Birkenbach et al.
6,063,570 A 5/2000 McGonigle et al.
6,150,502 A 11/2000 Strachan

OTHER PUBLICATIONS

Abe et al., J. Chem. Soc. Chem. Commun. 902-03 (1991).
Abe et al., 93 Chem. Rev. 2189-206 (1993).
Abe et al., 1 J. Chem. Soc. Perkin Trans. 783-91 (1994).
Altschul et al., 25(17) Nucl. Acids Res. 3389-402 (1997).
Caspi et al., 90(13) J. Am. Chem. Soc. 3563-64 (1968).
Choi et al., Accession No. Q59080 (1996).
Choi et al., Accession No. S58163 (1997).
Connor et al., 15(3) J. Protozool. 600-05 (1968).
Connor et al., 244(9) J. Biol. Chem. 2325-333 (1969).
Facciotti et al., Lipids in Photosynthesis: Structure, Function and Genetics 225-48 (1998).
Knutzon et al., 67 Soc. Exp. Biol. Semin. Ser. 287-304 (1998).
Murphy et al., 57 Soc. Exp. Biol. Semin. Ser. 95-130 (1998).
Napier et al., 2 Curr. Opin. Plant Biol. 123-27 (1999).
Perzl, Doctorial Dissertation (1996).
Poralla et al., 13(1) FEBS Lett. 107-10 (1980).
Saar et al., 1075 Biochimica et Biophysica Acta 93-101 (1991).
Wilson et al., 297 J. Mol. Biol. 233-49 (2000).
Nakashima et al., 274(15) J. Biol. Chem. 9976-9983 (1999).
Ochs et al., 174 Journal of Bacteriology 298-302 (1992).
Perzl et al., 143 Microbiology 1235-1242 (1997).
Wendt et al., 277 Science 1811-1815 (1997).

*Primary Examiner*—Charles L. Patterson, Jr.
(74) *Attorney, Agent, or Firm*—Hamilton, Brook, Smith & Reynolds, P.C.

(57) ABSTRACT

The present invention relates to nucleic acids isolated from Tetrahymena which code for a ciliate-specific triterpenoid cyclase. The inventive nucleotide sequences and the polypeptide sequences derived therefrom demonstrate a surprisingly minimal sequence identity to known isoprenoid cyclases. The invention also relates to the use of nucleic acids for the regulation of triterpenoid cyclase expression in a host organism, as well as the targeted knockout or repriming of the triterpenoid cyclase gene. As a result of the altered expression of the triterpenoid cyclase, it is possible to modify and enrich the levels of multiple unsaturated fatty acids in the host organism.

5 Claims, 10 Drawing Sheets

```
BLASTP 2.0.9 [May-07-1999]
Reference: Altschul, Stephen F., Thomas L. Madden, Alejandro A. Schaffer,
Jinghui Zhang, Zheng Zhang, Webb Miller, and David J. Lipman (1997),
"Gapped BLAST and PSI-BLAST: a new generation of protein database search
programs", Nucleic Acids Res. 25:3389-3402.Query= shc-ok_OGO   no
description
          (655 letters)Database: /LION/data/db/fast/nrdb
          415,815 sequences; 128,835,955 total letters
Searching..................................................done
                                                         Score      E
Sequences producing significant alignments:              (bits)   Value
pdb|1SQC|1SQC squalene-hopene cyclasebiological_unit: dimer    198    9e-50
swissnew|P33247|SQHC_ALIAC SQUALENE--HOPENE CYCLASE (EC 5.4.99....   198    9e-50
trembl|AB007002|AB007002_1 gene: "shc"; product: "Squalene-hope...   198    9e-50
trembl|X89854|AASHCGENE_1 gene: "shc"; product: "lanosterol syn...   196    5e-49
trembl|M73834|BASHC_1 gene: "squalene-hopene-cyclase"; product:...   196    5e-49
pdb|2SQC|2SQC-A squalene-hopene cyclaseMutantbiological_unit: h...   195    8e-49
pdb|3SQC|3SQC-A squalene--hopene cyclaseMutantbiological_unit: ...   195    1e-48
trembl|D90910|SSD910_105 gene: "shc"; product: "squalene-hopene...   168    2e-40
swiss|P33990|SQHC_ZYMMO SQUALENE--HOPENE CYCLASE (EC 5.4.99.-)....   149    7e-35
trembl|AL049485|SC6A5_13 gene: "SC6A5.13"; product: "putative s...   144    2e-33
swiss|P54924|SQHC_BRAJA SQUALENE--HOPENE CYCLASE (EC 5.4.99.-).      143    5e-33
trembl|X86552|BJDNASHC_4 gene: "shc"; product: "squalene-hopene...   143    5e-33
trembl|Y09979|RPSHCGEN_1 gene: "shc"; product: "squalene-hopene...   131    2e-29
swiss|P55348|SQHC_RHISN PROBABLE SQUALENE--HOPENE CYCLASE (EC 5...   126    6e-28
trembl|Y09978|MCSQSSHC_3 gene: "shc"; product: "squalene-hopene...   114    2e-24
trembl|AF027868|AF027868_60 gene: "sqhC"; product: "squalene-ho...    99    7e-20
trembl|U49919|ATU49919_1 product: "lupeol synthase"; Arabidops...     80    7e-14
trembl|AC002986|AC002986_41 gene: "YUP8H12R.42"; Arabidopsis t...     79    9e-14
trembl|U87266|U87266_1 product: "2,3-oxidosqualene-triterpenoid...    79    9e-14
trembl|Y15366|MTY15366_1 gene: "MtN18"; product: "cycloartenol ...    78    2e-13
swiss|P38605|CAS1_ARATH CYCLOARTENOL SYNTHASE (EC 5.4.99.8) (2,...    77    4e-13
trembl|AC005171|AC005171_11 gene: "T4E14.16"; product: "cycloar...    77    4e-13
trembl|AC005693|AC005693_1 gene: "T25N22.1"; product: "cycloart...    77    4e-13
pironly|A49398|A49398 cycloartenol synthase (EC 5.4.99.8) - Ara...    77    4e-13
trembl|AB025968|AB025968_1 gene: "GgCAS1"; product: "cycloarten...    76    6e-13
tremblnew|AB033335|AB033335_1 gene: "LcOSC2"; product: "oxidosq...    76    8e-13
trembl|AB009029|AB009029_1 gene: "OSCPNX1"; product: "Cycloarte...    74    3e-12
trembl|D89619|D89619_1 gene: "CASPEA"; product: "cycloartenol s...    71    2e-11
trembl|AB009031|AB009031_1 gene: "OSCPNZ1"; product: "Oxidosqua...    70    6e-11
tremblnew|AB025353|AB025353_1 gene: "ALLOSC1"; product: "oxidos...    69    8e-11
trembl|Z69727|SPAC4G9_21 gene: "erg7"; product: "lanosterol syn...    69    1e-10
swiss|Q10231|ERG7_SCHPO LANOSTEROL SYNTHASE (EC 5.4.99.7) (OXID...    69    1e-10
swiss|P38604|ERG7_YEAST LANOSTEROL SYNTHASE (EC 5.4.99.7) (OXID...    68    2e-10
trembl|U04841|SC04841_1 gene: "ERG7"; product: "lanosterol synt...    68    2e-10
trembl|U23488|SC23488_1 gene: "ERG7"; product: "2,3-oxidosquale...    68    2e-10
trembl|U10556|SCH9205_1 gene: "ERG7"; product: "Erg7p: 2,3-oxid...    68    2e-10
trembl|Z97338|ATFCA3_25 gene: "dl3730c"; product: "lupeol synth...    67    4e-10
trembl|AB009030|AB009030_1 gene: "OSCPNY1"; product: "beta-Amyr...    67    5e-10
trembl|AC002986|AC002986_43 gene: "YUP8H12R.44"; Arabidopsis t...     66    7e-10
tremblnew|AF169966|AF169966_1 gene: "CAS1"; product: "putative ...    66    9e-10
tremblnew|AB033334|AB033334_1 gene: "LcCAS1"; product: "cycloar...    65    2e-09
trembl|AB014057|AB014057_1 gene: "OSCPNY2"; product: "beta-Amyr...    64    3e-09
swiss|P48450|ERG7_RAT LANOSTEROL SYNTHASE (EC 5.4.99.7) (OXIDOS...    62    1e-08
trembl|U31352|RN31352_1 product: "oxidosqualene cyclase"; Ratt...     61    3e-08
swiss|P48449|ERG7_HUMAN LANOSTEROL SYNTHASE (EC 5.4.99.7) (OXID...    60    7e-08
trembl|AJ239031|HSA239031_1 gene: "LSS"; product: "lanosterol s...    60    7e-08
swiss|Q04782|ERG7_CANAL LANOSTEROL SYNTHASE (EC 5.4.99.7) (OXID...    57    3e-07
trembl|AC007260|AC007260_16 gene: "T30F21.16"; product: "Putati...    57    3e-07
trembl|Z97338|ATFCA3_22 gene: "dl3715c"; product: "lupeol synth...    57    6e-07
trembl|AC002986|AC002986_42 gene: "YUP8H12R.43"; Arabidopsis t...     51    3e-05
trembl|X87809|HSLANSTER_1 product: "lanosterol synthase"; H.sa...     40    0.065
```

Fig. 1

>trembl|X89854|AASHCGENE_1 gene: "shc"; product: "lanosterol synthase";
Alicyclobacillus acidoterrestris
Length = 634; Score = 196 bits (493), Expect = 5e-49
Identities = 166/589 (29%), Positives = 262/589 (44%), Gaps = 66/589 (11%)

```
Query:  85 LLQTQFEDGSWEQVREQNLETGQLDATVFNYWYLKSINNNPKIEAALQKARKWIVAQGGI 144
           ++ + EDG+W            L+ATV Y LK +    P  +  +A+++I  +GGI
Sbjct:  68 IISQRREDGTWSIYPGG---PSDLNATVEAYVALKYLGE-PASDPQMVQAKEFIQNEGGI 123

Query: 145 EATQTMTKFKLAAFGQYSWEDLWYVP---LFIFKQNGIFKYTYVKQIVAQWVYPHLTALA 201
           E+T+  T+  LA GQY W+ L  +P    + +K  Y +     A W    + L+
Sbjct: 124 ESTRVFTRLWLAMVGQYPWDKLPVIPPEIMHLPKSVPLNIYDF-----ASWARATIVTLS 178

Query: 202 YLRYQRTVFNVPVADLRELWINYPKNGIKISPREYSTLNPDSDLLILMDEIFKLK----- 256
           Y R++    +      + I  +   P+  S   DS  + +D+   K
Sbjct: 179 Y-RHESPTCDATSGLCKGSGIVRGEG----PPKRRSAKGGDSGFFVALDKFLKAYNKWPI 233

Query: 257 QPLGSFGAYTISTLLTLMSFKDFQS-----KHPHLYQNEIQKAYEDGYYFVEFNYFNFRE 311
           QP  G    L  +++ ++       + P Y    K        +      F  E
Sbjct: 234 QPGRKSGEQ--KALEWILAHQEADGCWGGIQPPWFYALLALKCLNMTDHPAFVKGFEGLE 291

Query: 312 AYHGSLDDGRW----------WDTILISWAMLESGQD-------KERIFPIVQNMVKEG-- 353
           AY   DG W            WDT L   A+  +G         K  +   + ++K+G
Sbjct: 292 AYGVHTSDGGWMFQASISPIWDTGLTVLALRSAGLPPDHPALIKAGEWLVSKQILKDGDW 351

Query: 354 -LQPKKGIGYGYDFEYA----PDTDDTGLLLVVMSYYKEAFQKQIPETI----EWLFSMQ 404
           ++  +K    G+ FE+     PD DDT +++ ++  +   +  + +       WL  MQ
Sbjct: 352 KVRRRKAKPGGWAFEFHCENYPDVDDTAMVVLALNGIQLPDEGKRRDALTRGFRWLREMQ 411

Query: 405 NDDGGYPAFDKGKNEDNLLFKFAFNMAGIANSAEIFDPSCPDITGHIMEGLGEFGYQANH 464
           + +GG+ A+D             F    A  S E+ DP   D+T H++E  G  FGY
Sbjct: 412 SSNGGWGAYDVDNTRQLTKSDSIF-----ATSGEVIDPPSEDVTAHVLECFGSFGYDEAW 466

Query: 465 PQIQNMIKYQRKTQNKWGSWQARWGVNYIMAVGAVVPGLARVNYDLNEQWVQNSINYLLN 524
           I+  ++Y +  Q     GSW  RWGVNY+   +GAVVPGL  V   D+ E WVQ S+++L+
Sbjct: 467 KVIRKAVEYLKAQQRPDGSWFGRWGVNYVYGIGAVVPGLKAVGVDMREPWVQKSLDWLVE 526

Query: 525 KQNKDGGFGECVLSYNDPEKWNGIGKSTVTQTSWGLLALLEVYNQEQIKHAADRAAQYL 584
            QN+DGG+GE    SY+DP +     G ST +QT+W  L+AL+            A R  YL
Sbjct: 527 HQNEDGGWGEDCRSYDDP-RLAGQGVSTPSQTAWALMALIA---GGRVESDAVLRGVTYL 582

Query: 585 LDQFKRDDNTFYDHSTIGTGHRGLLYLQYPSYAQSFPLVALNRYQKISQ 633
           D +R D ++      GTG G  YL Y   P+ AL RYQ+  Q
Sbjct: 583 HDT-QRADGGWDEEVYTGTGFPGDFYLAYTMYRDILPVWALGRYQEAMQ 630
```

Fig. 2A

```
>swissnew|P33247|SQHC_ALIAC SQUALENE--HOPENE CYCLASE (EC 5.4.99.-)
.//:swiss|P33247|SQHC_ ; Alicyclobacillus acidocaldarius
Length = 630; Score =  198 bits (499), Expect = 9e-50
Identities = 168/600 (28%), Positives = 273/600 (45%), Gaps = 95/600 (15%)

Query: 85   LLQTQFEDGSWEQVREQNLETG---QLDATVFNYWYLKSINNNPKIEAALQKARKWIVAQ 141
            LL Q EDG+W        L G    LD T+ Y LK I + + E +QKA ++I +Q
Sbjct: 67   LLHEQREDGTWA------LYPGGPPDLDTTIEAYVALKYIGMS-RDEEPMQKALRFIQSQ 119

Query: 142  GGIEATQTMTKFKLAAFGQYSWEDLWYVP---LFIFKQNGIFKYTYVKDIVAQWVYPHLT 198
            GGIE+++  T+  LA G+Y WE + VP   +F+ K+ +  Y +      W   +
Sbjct: 120  GGIESSRVFTRMWLALVGEYPWEKVPMVPPEIMFLGKRMPLNIYEF-----GSWARATVV 174

Query: 199  ALAYLRYQRTVFNVP----VADLRELWINYPKNGIK-------------ISPREYSTLNP 241
            AL+ + ++ VF +P     V +L E +  + G K             +  +  +++P
Sbjct: 175  ALSIVMSRQPVFPLPERARVPELYETDVPPRRRGAKGGGGWIFDALDRALHGYQKLSVHP 234

Query: 242  --DSDLLILMDEIFKLKQPLGSFGAYTISTLLTLMSFKDFQ-SKHPHLYQNEIQKAYEDG 298
              + + +D + + +   GS+G       L++ K   ++HP         A+    G
Sbjct: 235  FRRAAEIRALDWLLERQAGDGSWGGIQPPWFYALIALKILDMTQHP---------AFIKG 285

Query: 299  YYFVEFNYFNFREAYHGSLDDGRW---------WDTILISWAMLESGQ------------ 337
             + +E        Y   LD G W         WDT L   A+ +G
Sbjct: 286  WEGLEL--------YGVELDYGGWMFQASISPVWDTGLAVLALRAAGLPADHDRLVKAGE 337

Query: 338  ---DKERIFPIVQNMVKEGLQPKKGIGYGYDFEYAPDTDDTGLLLVVMSYYKEAFQKQ-- 392
               D++    P   + + L+P G  +D Y PD DDT +++ ++ +   +++
Sbjct: 338  WLLDRQITVPGDWAVKRPNLKPG-GFAFQFDNVYYPDVDDTAVVVWALNTLRLPDERRRR 396

Query: 393  --IPETIEWLFSMQNDDGGYPAFDKGKNEDNLLFKFAFNMAGIANSAEIFDPSCPDITGH 450
              + +   W+   MQ+ +GG+ A+D   N    D  N + +  E+ DP D+T H
Sbjct: 397  DAMTKGFRWIVGMQSSNGGWGAYDVDNTSD------LPNHIPFCDFGEVTDPPSEDVTAH 450

Query: 451  IMEGLGEFGYQANHPQIQNMIKYQRKTQNKWGSWQARWGVNYIMAVGAVVPGLARVNYDL 510
             ++E  G FGY  I+  ++Y ++ Q    GSW  RWGVNY+  GAVV  L V  D
Sbjct: 451  VLECFGSFGYDDAWKVIRRAVEYLKREQKPDGSWFGRWGVNYLYGTGAVVSALKAVGIDT 510

Query: 511  NEQWVQNSINYLLNKQNKDGGFGECVLSYNDPEKWNGIGKSTVTQTSWGLLALLEVYNQN 570
             E  ++Q ++++++   QN DGG+GE   SY DP  + G G ST +QT+W L+AL+
Sbjct: 511  REPYIQKALDWVEQHQNPDGGWGEDCRSYEDP-AYAGKGASTPSQTAWALMALIAGGRAE 569

Query: 571  EQIKHAADRAAQYLLDQFKRDDNTFYDHSTIGTGHRGLLYLQYPSYAQSFPLVALNRYQK 630
                AA R  QYL++  +R D + +     GTG G YL Y Y   FP +AL RY++
Sbjct: 570  SE---AARRGVQYLVET-QRPDGGWDEPYYTGTGFPGDFYLGYTMYRHVFPTLALGRYKQ 625
```

```
Tetrahymena      368  KA----PTDDIGLLLVESYYEEA--------FQK-CPPETIEWIFSIKNDQGCKPAFI
swissnew_P33247  366  PDVVYYPLVDDTAVVAWALNTLKGL--DP--PPFRL-PNTKLFRWIEGWQKSNGGWGAYI
trembl_X89854    367  FHCEKYPLVDDTMVVLAIKGICLI--DP--GKRRL-AITRLFRWIREMQKSNGGWGAYI
trembl_D90910    375  EDENFYPDIDDICVVMMALGGITLI--DP--EPKQG-AINSALCAIAIRKCKTGGWAAFI
trembl_AL049485  396  FHIDNYPDIDDTEVVLAIRRVFHH--IP--EPVEK-AIGRGVREINLGMQKKNGANGAFI
trembl_U49919    474  DRDHGAQVSICTFEALKCCLLLSVMSAIIGGQKIDKECLYDSWNLLLSLQKGNGCVNAWE Tetrahymena      415  KGKNECNLLEKFAFKMAGIANSELIFDISCPELIGHIMEGLEL-LYQAEHPQ-------I
swissnew_P33247  421  V---DNMSDLP---THIPHCLFGELTDPPLEDVTAHVLICFKSE--YDDAWKV------I
trembl_X89854    422  V---DNTRQLTK--SDSIFATSGEVIDPPREDVTAHVLICFKSE--YDEAWKV------I
trembl_D90910    430  I---DNDQDVL----CLEYGLLKAMIDISHACITAEVVMERAC-ILTMLSPR-------V
trembl_AL049485  451  V---DNMSAEP---HRLPHCLFSEVIDPPLADVTAHVVLMEAVE-ILAHLPE-------T
trembl_U49919    534  P---SRAYKMLELLNPTEEMAN-TWEREFVECTESVIKANDLRKLYEIHPKKEINRSI Tetrahymena      468  QNMEKLQEKTINKWGSYQARWGVIEIMEVGAVVIGELRINYLLNLQVAN-SINZILNK
swissnew_P33247  468  RRAVEYIEREIKPDGSWFGRWGVITLYTSTEPAVWSRIKAVLIITRELYIKI-AIDAEQH
trembl_X89854    470  FKAVEYIEACIRPDGSWFGRWGVIVVTLITAVVIGIKAVGVKMRELWVAL-SIDWLAEH
trembl_D90910    477  ENGITKILQELECDGSWFGRWGVIHILSIAVSAIIYDAQRFALKT-EIAWLLSC
trembl_AL049485  497  RPGKQWILDAKETDGSWFGRWGVNWYTGTIGSLEAATLAFLPTSHLARGLAVRWLELV
trembl_U49919    590  EKAVQFEQDNITPDGSWYINGLCEIEAMWFAEGSIAMALETYNECLAMRNGLHELLET Tetrahymena      527  KKQSPFKCVLSENELEKWNEIIK-SVEYTELGKLILLEVYNQNE-------QIKHLADI
swissnew_P33247  527  KPDGCWGEECRSKEDA-AYAAKA-STPSQTAWALMAILASHAS---------GEKARR
trembl_X89854    529  NEDGGWGEDCPRSIDDA-RLAACV-STPSQTAWALMAILASHAS---------SDALE
trembl_D90910    536  EADGGWGETHESIKEK-QLKCCKN-STASQTAWALLGILDRLSYLPSLGQDAKLHTAIEG
trembl_AL049485  556  EEDGGWGEILRSERYVREWSERIA-STASQTGMALHALLKAAERE---------SKAVE
trembl_U49919    650  RDDGGWGHESYLLCSEQRYIPSELERNLVQTSMAMMALHTKQAER-------DLTPLHL Tetrahymena      580  HACYLILQFKKDRNEIYEHSTIGTIHRILLAIQKPSLAISLPIVAKNKICSISQGQYHFS
swissnew_P33247  576  SICYIVEM--EPCRGVDEPYITGTFFFGDFYLGLTIEHVFEILALGRIKQAIERR----
trembl_X89854    578  LIVFHLR--HAEIGVDEEVYTGTCFFGDFYLATMICDELSVWALGRIQEAIQRIRG--
trembl_D90910    594  GIAEILQG-TPKSTREIAEYTGTGFICHEYIREHYIR-YFPLIAIARISELQAS-----
trembl_AL049485  606  GVAEIAAFE-ELGSWDEPYSTGTGFIVMISENINLYRLVFIITALGRIVGEPFAKKPR
trembl_U49919    703  EAKLEINSE-LBNIDEPQQEIVIESMNTCMEHLATYPLTFPIWALEERKVIFIVN---

Tetrahymena      640  KNLYNGNGEPVQKQNI
swissnew_P33247       ----------------
trembl_X89854         ----------------
trembl_D90910         ----------------
trembl_AL049485  665  AADAPAEAAPAEVKGS
trembl_U49919         ----------------
```

Fig. 3 (continued)

NUCLEIC ACID ISOLATED FROM *TETRAHYMENA* WHICH CODES FOR A TRITERPENOID CYCLASE, ITS PRODUCTION, AND USE

CROSS REFERENCE TO RELATED APPLICATIONS

The present application is a divisional of and claims, under 35 U.S.C. § 120, the benefit of U.S. patent application Ser. No. 09/725,735, filed 30 Nov. 2000, now U.S. Pat. No. 6,645,751 which is expressly incorporated fully herein by reference.

FIELD OF THE INVENTION

The present invention relates to a triterpenoid cyclase (tetrahymanol cyclase) isolated from *Tetrahymena*, its coding nucleic acid, its production, and use.

BACKGROUND OF THE INVENTION

The inventive triterpenoid cyclase catalyzes the formation of tetrahymanol from squalene by a direct cyclization of squalene (Capsi et al. (1968) J. AM. CHEM. SOC. 90:3563–3564; Abe et al. (1993) CHEM. REV. 93:2189–2206). The triterpenoid cyclase also recognizes oxidosqualene as a substrate (Abe & Rohmer (1994) J. CHEM. SOC. PERKIN TRANS. 1: 783–791). In addition to pentacyclic triterpenoids, the squalene tetrahymanol cyclase also catalyzes the formation of tetracyclic triterpenoids (Abe & Rohmer (1991) J. CHEM. SOC. CHEM. COMMUN. 902–903). Tetrahymanol (or gammaceran-3-ol), which is derived from isoprene, is a member of the isoprenoid class. Isoprenoids play an important role as phytohormones and carotenoids, and as components of chlorophyll, ubiquinone, plant resins, oils, and latex. As steroid hormones, isoprenoids effect important functions in animals. The formation of tetrahymanol can be reprimed in *Tetrahymena* by adding sterols, such as cholesterol (Conner et al. (1968) J. PROTOZOOL. 15:600–605; Conner et al. (1969) J. BIOL. CHEM. 244:2325–2333).

Isoprenoids are also important components of bacterial and eukaryotic membranes. Similar to hopanoids and sterols (such as cholesterol), pentacyclic triterpenoid has tetrahymanol membrane-stabilizing properties (Conner et al. (1968; 1969); Poralla et al. (1980) FEBS LETT. 113:107–110). By restricting the fluidity of the lipid acid residues of membrane lipids, a condensed (membrane-solidifying) effect is achieved above the phase transition temperature; while below the phase transition temperature, the fluidity of the membrane is increased, thus preventing the optimal close packing of fatty acid residues. In addition, the membrane fluidity depends on the fatty acid composition of the membrane lipids. The fluidity of membranes increases in proportion to the levels of unsaturated fatty acids. With temperature changes, organisms are able to regulate the fluidity of their membranes, for example, via the fatty acid composition. Below the phase transition temperature, isoprenoids and unsaturated fatty acids increase the membrane fluidity via a synergistic effect. The inhibition of the synthesis of the cyclic triterpenoids alters membrane stability. This reduced membrane fluidity can be compensated by an increased proportion of polyunsaturated fatty acids (PUFAs) in the membrane, i.e., the content of PUFAs can be increased by inhibition of the triterpenoid cyclase.

The targeted modification of the composition of the fatty acid spectrum by means of gene technology for the commercial production of special fatty acids or oils is described in Napier et al. (CURR. OPIN. PLANT BIOL. (1999) 2:123–127); Murphy & Piffanelli (SOC. EXP. BIOL. SEMIN. (1998) Ser. 57 (PLANT LIPID BIOSYNTHESIS) 95–130); and FACCIOTTI & KNAUF (In: ADV. PHOTOSYNTH. 6: LIPIDS IN PHOTOSYNTHESIS: STRUCTURE, FUNCTION AND GENETICS. Siegenthaler & Murata (eds.) Kluwer Academic Publishers, Netherlands. (1998) 225–248). Thus, the modification of fatty acid composition can be regulated by altering the genes that code for enzymes which directly participate in the fatty acid synthesis, such as desaturases. However, it has been reported that the level of PUFAs in transgenetic organisms was relatively low (Knutzon & Knauf (1998) SOC. EXP. BIOL. SEMIN. SER. 67:287–304).

The knockout or repriming of the gene that codes for triterpenoid cyclase and the resulting deficiency of tetrahymanol may influence membrane fatty acid composition. However, the modified membrane fluidity can be balanced by the production of unsaturated fatty acids.

Although the triterpenoid cyclase protein from *Tetrahymena* is known and has been purified (Saar et al. (1991) BIOCHEM. BIOPHYS. ACTA, 1075:93–101), it had not been possible to clone the gene for triterpenoid cyclase from *Tetrahymena* (dissertation of Michal Perzl (1996) at the Faculty of Biology of Eberhard Karls University Tübingen). In previous studies, the gene sequence of triterpenoid cyclase could not be determined by sequencing the purified protein, PCR with degenerative primers, or hybridization with heterologous probes.

The present invention relates to nucleic acids isolated from *Tetrahymena* which code for a ciliate-specific triterpenoid cyclase. The inventive nucleotide sequences and the polypeptide sequences derived therefrom demonstrate a surprisingly minimal sequence identity to known isoprenoid cyclases. The invention also relates to the use of nucleic acids for the regulation of triterpenoid cyclase expression in a host organism, as well as the targeted knockout or repriming of the triterpenoid cyclase gene. As a result of the altered expression of the triterpenoid cyclase, it is possible to modify and enrich the levels of multiple unsaturated fatty acids in the host organism.

SUMMARY OF THE INVENTION

The present invention is directed to an isolated nucleic acid comprising a nucleic acid sequence encoding a polypeptide or functional variant thereof comprising the amino acid sequence of SEQ ID No. 12.

In a preferred embodiment, the isolated nucleic acid of the present invention comprises the nucleic acid sequences of SEQ ID No. 11 and SEQ ID No. 13. In another embodiment of the present invention, the isolated nucleic acid comprises at least 8 nucleotides of SEQ ID No. 11. Another embodiment is an isolated nucleic acid of the present invention wherein the nucleic acid is selected from the group comprising DNA, RNA, and double-stranded DNA. In yet another embodiment of the invention, the isolated nucleic acid comprises one or more non-coding sequences.

In one aspect of the invention, the isolated nucleic acid is antisense. Another aspect relates to a vector comprising the isolated nucleic acid of the present invention, preferably the vector is an expression vector. In addition, the invention is also directed to isolated host cells comprising said vector. Preferably, the host cells are protozoan, in particular, ciliate.

Another embodiment is a method of producing the isolated nucleic acid of the present invention comprising the step of chemically synthesizing said nucleic acid. An additional embodiment is a method of producing the isolated nucleic acid comprising the step of isolating said nucleic acid from a gene library by screening said library with a probe.

The present invention also relates to an isolated polypeptide or functional variant thereof comprising the amino acid sequence of SEQ ID No. 12. In particular, the invention relates to an isolated polypeptide comprising at least 6 amino acids of SEQ ID No. 12.

Also within the scope of the present invention is a method of producing a polypeptide comprising culturing a host cell under conditions sufficient for the production of said polypeptide and recovering said polypeptide from the culture. The host cell may be a protozoa, preferably a ciliate.

One aspect of the present invention is directed to an antibody capable of binding the polypeptide of SEQ ID No. 12. Another aspect of the present invention relates to a method of producing said antibody of comprising the steps of immunizing a mammal with a polypeptide and isolating said antibodies.

In one embodiment of the present invention, the isolated nucleic acid is used to identify polypeptide variants comprising the steps of screening a gene library with said nucleic acid and isolating said variant.

Also within the scope of the present invention is a method of enriching the squalene content, in a host cell comprising the step of inactivating the inventive nucleic acid. The nucleic acid may be inactivated by an antisense nucleic acid, by a deletion or insertion of a nucleic acid sequence, or mutation of said nucleic acid sequence. In particular, the inventive nucleic acid may be replaced with one or more selectable markers.

In another embodiment of the present invention, the isolated nucleic acid is used to produce cyclic triterpenoids, preferably pentacyclic triterpenoids, and most preferred tetrahymanol.

BRIEF DESCRIPTION OF THE DRAWINGS

FIG. 1. Results of a BLASTP database comparison of the protein sequence according to SEQ ID No. 12 with protein databases.

FIG. 2A. Alignment of the protein sequence according to SEQ ID No. 12 with known pentacyclic triterpenoid cylcases, lanosterol synthesis isolated from *Alicyclobacillus acidoterrestris* (SEQ ID No. 14).

FIG. 2B. Alignment of the protein sequence according to SEQ ID No. 12 with known pentacyclic triterpenoid cyclases, squalene-hopene cyclase isolated from *Alicyclobacillus acidoterrestris* (SEQ ID No. 15)

FIG. 3. Multiple alignment of the polypepetide sequence according to SEQ ID No. 12 from *Tetrahymena* with known pentacyclic triterpenoid cyclases (SEQ ID Nos. 16–20).

DETAILED DESCRIPTION OF THE INVENTION

The present invention relates to nucleic acids isolated from *Tetrahymena* which code for a ciliate-specific triterpenoid cyclase. The inventive nucleotide sequences and the polypeptide sequences derived therefrom demonstrate a surprisingly low sequence identity to known isoprenoid cyclases. Another aspect of the invention is the genomic nucleotide sequence of the triterpenoid cyclase, which in addition to the coding sequence, contains non-coding nucleotide sequences, such as introns, promoters, and flanking sequences. The invention also relates to the use of nucleic acids for regulating expression, targeted knockout, or repriming of this gene. By regulating the expression of the triterpenoid cyclase, it is possible to modify the levels of multiple unsaturated fatty PUFAs in an organism. Moreover, as a result of the targeted knockout of triterpenoid cyclase, an enrichment of squalene, an intermediate in the synthesis of various triterpenoids, can be achieved. Squalene serves as a synthetic module for terpenes. Partially modified squalene (e.g., in hydrogenated form) is used in dermatology products and cosmetics, as well as in various derivatives found in skin and hair care products. In a further embodiment, a targeted overexpression of the inventive nucleic acids may result in the production of cyclic triterpenoids such as pentacyclic triterpenoids (e.g., tetrahymanol or hopane), and tetracyclic triterpenoids (e.g., lanosterol or cycloartenol). Cyclic triterpenoids are used in the synthesis of steroid hormones and saponins. These compounds display good skin penetration and diffusion properties, and therefore, they are also used in cosmetics and dermatology products.

The inventive nucleic acids can be isolated from ciliates, preferably *Tetrahymena*, and most preferred from *Tetrahymena thermophila*.

One aspect of the present invention is to provide a nucleic acid isolated from *Tetrahymena*, which codes for a polypeptide with the activity of a triterpenoid cyclase. Another aspect of the invention is the regulation of gene expression or genetic knockout (adequate inhibition) of the triterpenoid cyclase in a host organism, preferably in *Tetrahymena*, in order to increase the level of PUFAs produced in the organism. In particular, a further aspect is to enrich the levels of gamma-linolenic acid (GLA) by means of the host's own production of PUFA for restoration of membrane stability.

Figure 4:
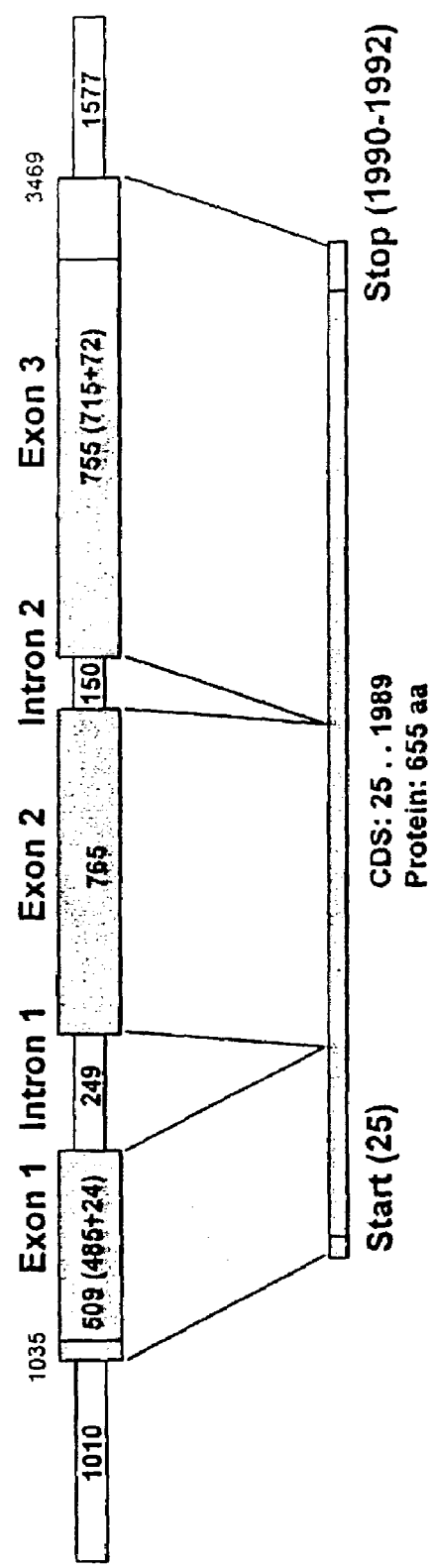
FIG. 4. Schematic diagram of the gene structure of triterpenoid cyclase from *Tetrahymena* according to SEQ ID No. 11 and SEQ ID No. 9.
Figure 5:
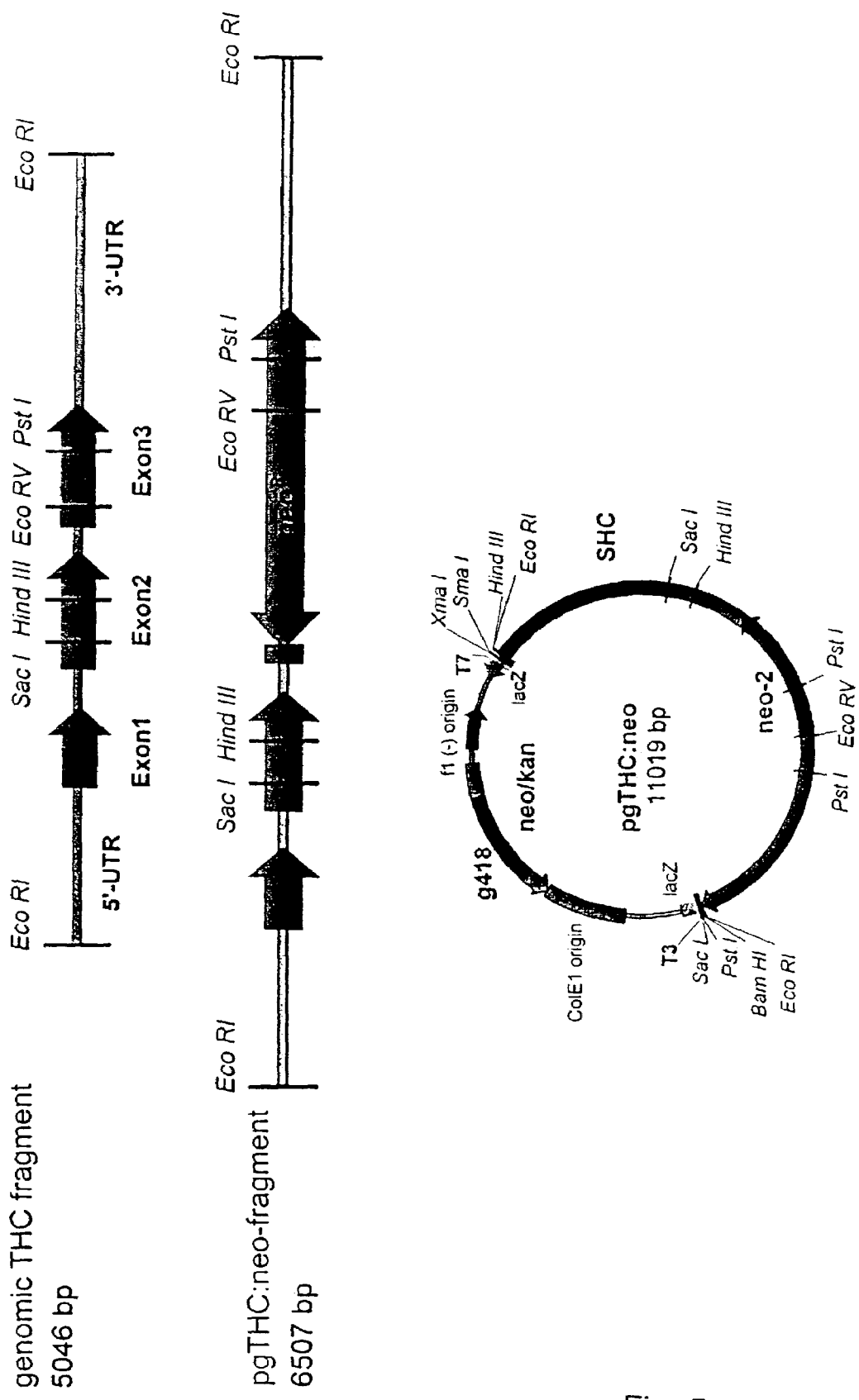
FIG. 5. Schematic diagram of the triterpenoid knockout construct. A neo-cassette plasmid was inserted into the genomic sequence of *Tetrahymena* to produce the genetic knockout. The construct contains a neomycin resistance gene regulated by the *Tetrahymena* histone H4 promoter and the 3' flanked sequence of the BTU2 (β-tubulin 2) gene. The neo-cassette plasmid was digested with EcoRV and Sma I. The resulting 1.4 kb fragment was then ligated into the EcoRV-digested plasmid pgTHC producing the plasmid pgTHC::neo.

A further embodiment of the present invention is the nucleic acids according to SEQ ID No. 11 and SEQ ID No. 13, which code for a triterpenoid cyclase with the amino acid sequence according to SEQ ID No. 12 or a functional variant thereof, and fragments thereof with at least 8 nucleotides, preferably with at least 15 or 20 nucleotides, in particular, with at least 100 nucleotides, and most preferred, with at least 300 nucleotides (hereinafter called "inventive nucleic acid(s)"). The nucleic acid according to SEQ ID No. 11 represents the protein-coding (or cDNA) sequence. The nucleic acid, according to SEQ ID No. 13, represents a genomic sequence of the triterpenoid cyclase, which in addition to the coding sequence, also contains non-coding nucleic acid sequences such as introns, promoters, and flanking sequences (such as UTR) (FIG. 4).

Figure 3:
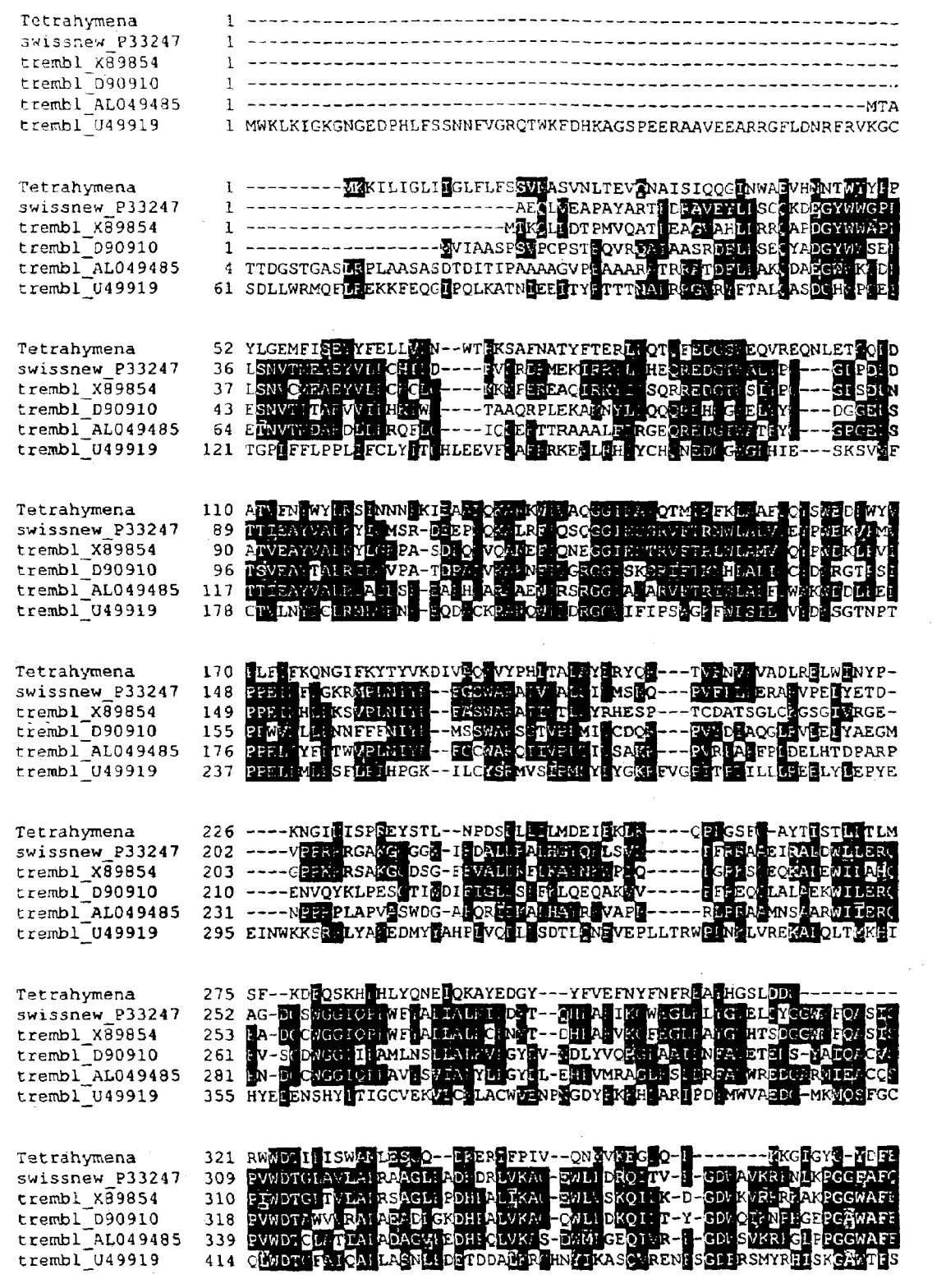

The complete nucleic acid sequence according to SEQ ID No. 11 codes for a protein with 655 amino acids and a theoretical molecular mass of 76.02 kDa. Sequence analysis, as provided in the present invention, confirms that the nucleic acid codes for the pentacyclic triterpenoid cyclase isolated from *Tetrahymena*. A homology comparison enabled the identification of the protein sequence as a triterpenoid cyclase according to SEQ ID No. 12, which is derived from the nucleic acid sequence (SEQ ID No. 11). A BLASTP search (Altschul et al. (1997) NUCLEIC ACID RES. 25:3389–3402) was used for the homology comparison. Isopenoid cyclases (such as squalene-hopene cyclase, and lanosterol and cycloartenol synthetases) were identified as homologous proteins from the database (FIG. 1). The known triterpenoid cyclases (SEQ ID Nos. 14–15) have a maximum identity of 28% as compared to the inventive polypepetide sequence (FIG. 2). A multiple alignment of various known isopenoid cyclases (SEQ ID Nos. 16–20) and the inventive polypeptide sequence is shown in FIG. 3. Homologies are observed in the conserved domains. One such domain is the QW-motif (K/R $X_{2-3}$ F/Y/W L $X_3$ Q $X_{2-5}$ G X W (SEQ ID No. 21); Poralla et al. (1994) TRENDS IN BIOCHEM. SCI. 19:157–158; Poralla (1994) BIOORG. MED. CHEM. LETT. 4:285–290), which occurs seven to eight times in squalene-hopene cyclases, and seven times in oxidosqualene cyclases. The inventive polypeptide sequence has seven such QW-motifs, which are distinctly less conserved as compared to other known triterpenoid cyclases. Another conserved motif is the aspartate-rich motif (D V/L D D T A (SEQ ID No. 22); (Perzl et al. (1997) MICROBIOLOGY 143: 1235–1242), which is less conserved in the inventive polypeptide sequence in the homologous position (D T D D T G (SEQ ID No. 23)). Similar aspartate-rich motifs were found in other enzymes of the isopenoid biosynthesis pathway (ASHBY ET AL. (1990) in: MOLECULAR BIOLOGY OF ATHEROSCHLEROSIS, 27–34. Ed. AD Attie, Amsterdam, Elsevier). While the inventive polypeptide sequence has been identified as triterpenoid cyclase, it differs considerably from other cyclases. The overall identity of the inventive polypeptide sequence as compared to known cyclases is surprisingly small.

In a preferred embodiment, the inventive nucleic acid is a DNA or RNA molecule, preferably a double-stranded DNA molecule, or a functional variant, of the nucleic acid sequence according to SEQ ID No. 11, or the genomic nucleic acid sequence according to SEQ ID No. 13.

According to the present invention, the term "functional variant" is defined as a nucleic acid which is functionally related to the triterpenoid cyclase isolated from *Tetrahymena*, such as other pentacyclic triterpenoid cyclases, or allelic or degenerate variants.

In a narrower sense, according to the present invention, the tern "variant" is defined as nucleic acids, which have a sequence identity of approximately 60%, preferably of approximately 75%, in particular, of approximately 90%, and most preferred, of approximately 95%. In this case, the degree of hybridization must also be taken into consideration.

The invention also comprises functional variants of the nucleic acid, which include nucleotide changes that do not alter the protein sequence. Due to the unusual codon use by ciliates (Wuitschick & Karrer (1999) J. EUKARYOT. MICROBIOL. 46(3):239–247), the described DNA sequence must be modified for expression in other systems. For example, codons TAA and TAG, which code for glutamine in ciliates and are stop codons in most other systems, are replaced with the codons CAA and CAG for expression in other organisms. In addition, by modifying the sequence to the respective codon preference (or codon usage) of various organisms, protein expression can be optimized in these organisms. Modification of nucleic acid sequences can be accomplished using methods well known to one skilled in the art. Alternatively, the sequence can be generated by chemically synthesizing oligonucleotides. The specific base changes in the nucleic acid sequence can be determined utilizing known codon usage tables of the preferred expression systems (i.e., Codon usage tabulated from the gene library: http://www.dna.affrc.go.jp/~nakamura/CUT-G.html). The present invention also comprises variants of nucleic acids.

The variants or fragments of the inventive nucleic acids can be used as probes to identify additional functional variants, or as antisense nucleic acids. For example, a nucleic acid of at least approximately 8 nucleotides is suitable as an antisense nucleic acid; a nucleic acid of at least approximately 15 nucleotides as primer for PCR; a nucleic acid of at least approximately 20 nucleotides is suitable for identifying other variants; and a nucleic acid of at least approximately 100 nucleotides is may be used as a probe.

In a preferred embodiment, the protein-coding sequence of the inventive nucleic acid is deleted or replaced with a selectable gene, such as a gene for antibiotic resistance. Using this approach, the native gene can be "knocked out" in a host organism (gene knockout) by homologous recombination. By replacing or deleting the triterpenoid cyclase gene, the synthesis of cyclic triterpenoids is inhibited resulting in a modification of the fatty acid composition in the host organism. In another aspect of the present invention, the inventive nucleic acid sequence is altered by a deletion, insertion, or point mutation leading to either a reduced or an increased activity of triterpenoid cyclase.

In another embodiment, the triterpenoid cyclase isolated from *Tetrahymena* is expressed in another host cell or organism. To accomplish expression in another host, the inventive nucleic acid is ligated into a vector, preferably in an expression vector.

The expression vectors can be either prokaryotic or eukaryotic expression vectors. For prokaryotic expression, the T7 expression vector, pGM10, (Martin, 1996) can be expressed in *E. coli* cells. This vector contains an N-terminal "histidine tag" sequence (Met-Ala-His$_6$) which can be used for protein purification by Ni2+-NTA affinity chromatography. The eukaryotic expression vectors, p426Met25 and p426GAL1 (Mumberg et al. (1994) NUCL. ACIDS RES., 22:5767–68) are suitable for the expression in *Saccharomyces cerevisiae*. In insect cells, Baculovirus vectors such as EP-BI-0127839 or EP-B1-0549721 may be used for protein expression, and for expression in mammalian cells, SV40 vectors may be utilized. For detailed information concerning suitable vectors, refer to SAMBROOK ET AL. (1989) MOLECULAR CLONING: A LABORATORY MANUAL, Cold Spring Harbor Laboratory, Cold Spring, N.Y.; Goeddel, ed. (1990) METHODS IN ENZYMOLOGY 185 Academic Press; and PERBAL (1988) A PRACTICAL GUIDE TO MOLECULAR CLONING, John Wiley and Sons, Inc. The recombinant proteins or fragments thereof can be isolated by methods of protein purification that are well known to one skilled in the art (e.g., AUSUBEL ET AL. (1995), CURRENT PROTOCOLS IN MOLECULAR BIOLOGY, Green Publishing Associates, New York).

The expression vectors preferably contain sequence elements which influence expression, such as promoters, enhancer elements, and "upstream" activating sequences. Inducible and constitutive promoters, as well as tissue-specific promoters, are suitable for expression of the inventive nucleic acids. For example, the cauliflower mosaic virus (CaMV) 35S promoter (Restrepo et al. (1990) PLANT CELL 2:987–98) or promoters which are activated during seed development, are suitable for the expression in plant cells.

In a preferred embodiment of the present invention, the vectors used for expression of the inventive nucleic acids are shuttle vectors (Wolk et al. (1984) PROC. NATL. ACAD. SCI. USA, 81:1561–1565; and Bustos et al. (1991) J. BACTERIOL. 174:7525–7533).

Generally, the expression vectors also contain regulatory sequences which are compatible with the host cell, such as the trp promoter for the expression in *E. coli* (refer to EP-B1-0154133), the ADR2 promoter for the expression in yeast (Russel et al. (1983), J. BIOL. CHEM. 258:2674–82), the Baculovirus polyhedrin promoter for the expression in insect cells (refer to EP-B1-0127839), or the early SV40 promoter or LTR promoters of MMTV (Mouse Mammary Tumor Virus; Lee et al. (1981) NATURE, 294:228–32) for mammalian expression.

Vectors, which contain the inventive nucleic acid sequence, can be transferred to cells by infection, transfection, electroporation, particle bombardment, and other methods known to those skilled in the art. According to the present invention, transformation is generally defined as the introduction of nucleic acids into a host cell (Sambrook et al. 1989; Potrykus (1991) ANNU. REV. PLANT PHYSIOL. PLANT MOL. BIOL. 42:205–225; Christou (1993) CURR. OP. BIOTECH. 4:135–141).

In another aspect, the expression vector contains the inventive nucleic acids in functional combination with promoters or other regulatory elements, or in combination with another gene. Preferably the additional gene is a selection marker, such as a gene for antibiotic resistance. In a preferred embodiment, the regulatory elements are nucleic acid sequences which are functionally active in ciliates, and in particular, active in *Tetrahymena*.

In another embodiment of the present invention, the inventive nucleic acid is expressed in *Tetrahymena* under the regulation of a strong promoter, such as the *Tetrahymena* tubulin promoter (Gaertig et al., (1999) NATURE BIOTECH. 17: 462–465). Preferably, the transformation of *Tetrahymena* may be achieved according to the methods described by Gaertig et al. (1999); Gaertig & Gorovsky (1992) PROC. NATL. ACAD. SCI. USA 89:9196–9200. In another aspect, the regulatory elements for expression may be the promoters for α- or β-tubulin isolated from *Tetrahymena thermophila*. The transformed *Tetrahymena* may be identified using a selection media, such as a media that contains an antibiotic.

Overexpression of the inventive nucleic acids may result in the production of cyclic triterpenoids, preferably pentacyclic triterpenoids, and most preferred tetrahymanol.

The inventive nucleic acids can be chemically synthesized based on the sequences disclosed in SEQ ID No. 11 and 13, or based on the peptide sequence disclosed in SEQ ID No. 12 according to the phosphotriester method (Uhlman & Peyman (1990) CHEMICAL REVIEWS, 90:543, No. 4). The inventive nucleic acids may also be isolated from an appropriate cDNA or genomic library generated from an organism possessing isoprenoid cyclase activity (Sambrook, et al., 1989). Single-stranded DNA fragments derived from the nucleic acid sequences according to SEQ ID No. 11 or 13 with a length of approximately 100–1000 nucleotides, preferably with a length of approximately 200–500 nucleotides, and most preferred, with a length of approximately 300–400 nucleotides may be suitable as probes to screen a cDNA or genomic library.

Another embodiment of the present invention is a polypeptide with an amino acid sequence according to SEQ ID No. 12, or a functional variant thereof. Another aspect is amino acid fragments according to SEQ ID No. 12 with at least six amino acids, preferably with at least 12 amino acids, in particular, with at least 65 amino acids, and, most preferred, with at least 150 amino acids (hereinafter called "inventive polypeptide"). In addition, polypeptides with a length of approximately 6–12 amino acids, preferably approximately 8 amino acids, may contain an epitope. The epitope may be coupled with a carrier and then may be used for the production of polyclonal or monoclonal antibodies (see e.g., U.S. Pat. No. 4,656,435). Polypeptides with a length of at least approximately 65 amino acids may also be used directly, without a carrier, to produce polyclonal or monoclonal antibodies.

Within the meaning of the present invention, the term "functional variant" is defined as a polypeptide which is functionally associated with the inventive peptide, i.e., it exhibits triterpenoid cyclase activity.

Also within the meaning of the present invention, the term "variant" includes polypeptides which have sequence homology. In particular, variant includes polypeptides with a sequence identity of approximately 70%, preferably approximately 80%, in particular, approximately 90%, and most preferred, approximately 95% compared to the protein with the amino acid sequence according to SEQ ID No. 12.

In another aspect, the term variant includes deletions of the polypeptide in the range of approximately 1–60 amino acids, preferably approximately 1–30 amino acids, in particular, approximately 1–15 amino acids, and most preferred, approximately 1–5 amino acids. For example, methionine, the first amino acid of a protein, may be deleted without appreciably altering the function of the polypeptide.

Another embodiment of the present invention includes fusion proteins, which contain the above-described inventive polypeptides. The fusion proteins may possess triterpenoid cyclase activity, or may gain the activity after the removing a portion of the fusion moiety. These fusion proteins contain, in particular, non-ciliated sequences of approximately 1–200 amino acids, preferably approximately 1–150 amino acids, in particular, approximately 1–100 amino acids, and most preferred, approximately 1–50 amino acids. Examples of non-ciliated peptide sequences include prokaryotic peptide sequences such as galactoidase or a histidine tag (i.e., Met-Ala-His$_6$ tag). The fusion protein containing a histidine tag is particularly advantageous for purifying the expressed protein by affinity chromatography using metal ion-containing columns such as an Ni2+ NTA column (NTA: chelating nitrilotriacetic acid).

In a further aspect of the present invention includes variants of the inventive polypeptide which serve as epitopes that can be specifically identified by antibodies.

The inventive polypeptide can be produced, for example, by expressing the inventive nucleic acid in a suitable expression system according to methods which are generally known to a person skilled in the art. Strains of *E. coli* (DH5, HB101 or BL21), yeast (*Saccharomyces cerevisiae*), insect cell lines (Lepidopteran species: *Spodoptera frugiperda*), or animal cells (COS, Vero, 293, and HeLa) are commercially available and suitable as host cells.

In another embodiment, peptide variants of the polypeptide can be synthesized by classical peptide synthesis methods (i.e., Merrifield Technique). These peptides can be used to produce antisera that can then be utilized to screen gene expression libraries as a means to identify additional functional variants of the inventive polypeptide.

Another aspect of the present invention relates to a method for producing an inventive polypeptide by expressing an inventive nucleic acid in a suitable host cell, and if appropriate, isolating the inventive polypeptide.

The present invention also relates to antibodies which specifically react with the inventive polypeptide, in particular where variants of the polypeptide are either immunogenic or are rendered immunogenic by coupling a suitable carrier, such as bovine serum albumin, to the variant. The antibodies of the present invention may be either polyclonal or monoclonal.

The method of producing antibodies is another aspect of the present invention. Antibodies can be generated according to methods generally known in the art. For example, a mammal, such as a rabbit, may be immunized with the inventive polypeptide or variant thereof, and if appropriate, in the presence of an adjuvant (e.g., Freund's adjuvant or aluminum hydroxide gels) (Diamond et al. (1981) N. ENGL. J. MED., 304:1344–49). The polyclonal antibodies produced in the animal as a result of the immunological response, can easily be isolated from blood using methods generally known in the art. For example, antibodies may be purified by column chromatography. A preferred method of antibody purification is affinity chromatography, for example, the HiTrap™ NHS-activated columns (Pharmacia, Piscataway, N.J.). Monoclonal antibodies can be produced according to the methods described by Winter & Milstein (Winter & Milstein, (1991) NATURE, 349:293–99).

In a preferred embodiment, the inventive nucleic acids are used to produce a genetic knockout of triterpenoid cyclase in a host organism, preferably *Tetrahymena*. As a result of this gene knockout, the levels of PUFA, in particular, GLA, are increased in the host organism. A gene knockout in *Tetrahymena* can be accomplished by homologous recombination wherein a nucleic acid according to SEQ ID No. 11 or 13 is modified by replacing the protein-coding sequence with a selectable gene (e.g., an antibiotic resistant gene) (Gaertig et al. (1994) NUCL. ACIDS RES. 22:5391–5398; Kahn et al. (1993) PROC. NATL. ACAD. SCI. USA 90:9295–9299). In addition to gene knockout technology (Galli-Taliadoros (1995) J. IMMUNOL. METHODS 181:1–15), an antisense strategy (Atkins et al. (1994) BIOL. CHEM. HOPPE SEYLER 375:721–729) or the antisense ribosome method (Sweeney et al. (1996) PROC. NATL. ACAD. SCI. USA 93:8518–8523) may be utilized to reduce activity of triterpenoid cyclase.

The inventive nucleic acids of the present invention code for a ciliate-specific triterpenoid cyclase isolated from *Tetrahymena*. These nucleic acids can be used to generate transgenic organisms, preferably *Tetrahymena*, which contain an increased level of unsaturated fatty acids. In a preferred embodiment of the present invention, the inventive nucleic acids may be utilized in the commercial production of PUFAs, in particular, GLA. In another embodiment, the GLA content of the transgenic organism (i.e., a transgenic *Tetrahymena*) may be increased by the combination of a genetic knockout (or reduction) of tetrahymanol cyclase activity and a functional overexpression of fatty acid desaturase.

In a preferred embodiment, a host organism, preferably *Tetrahymena*, is transformed with the inventive nucleic acid or the above-described structures (Gaertig et al. (1999); Gaertig & Gorovsky (1992); Gaertig et al. (1994); Kahn et al. (1993) PROC. NATL. ACAD. SCI. USA 90:9295–9299).

The transformed *Tetrahymena* may be grown and enriched in a selective media, and then lipid(s) may be isolated from these cells according to standard methods (e.g., Dahmer et al., (1989) J. AM. OIL CHEM. SOC. 66:543). The methyl esters of fatty acids can be analyzed by gas chromatography.

The inventive nucleic acids or variants thereof can also be used to identify related genes from other organisms, in particular, from other protozoa or protista, preferably ciliates (systematized according to Cavalier Smith (1995) ARCH. PROTISTENK. 145:189–207). The inventive nucleic acid or variants thereof can be used as a labeled probe for isolating homologous genes. By hybridizing the labeled probe with isolated nucleic acids or other organisms, homologous nucleic acid sequences may be detected and isolated. The nucleic acid probe can be labeled in a manner known to the person skilled in the art (Ausubel et al., 1995; Sambrook et al., 1989). For example, radioactive nucleotides or nucleotides linked to detectable molecules, such as fluorophores, digoxigenin, biotin, magnetic molecules or enzymes, may be used to label the nucleic acid probe. Homologous DNA sequences may be identified by hybridization of the labeled probe. Genomic or cDNA libraries may be used to screen for homologous sequences. In addition, Southern and Northern blots may also be used to identify homologous sequences. Alternatively, homologous DNA may be hybridized with a labeled probe, and isolated by selective retention of the labeled probe (e.g., a magnet).

Homologous genes can also be isolated and cloned by means of cross-hybridization, using methods which are known to a person skilled in the art, as described, for example, in Ausubel et al. (1995), or Sambrook et al. (1989).

Oligonucleotides can be generated based on an isolated DNA sequence which represents the protein coding sequence and these oligonucleotides can then be used to identify additional homologous nucleic acid sequences by polymerase chain reaction (PCR).

Detection with specific antibodies against the protein or variants thereof (such as peptide antibodies) coded by the nucleic acid sequence of the present invention, provides another option for isolating homologous proteins.

A plurality of well-established methods such as the methods described in Sambrook et al. (1989) are well known in the art for isolating genomic DNA and mRNA, as well as for producing genomic and cDNA libraries.

EXAMPLES

The following examples serve to illustrate the invention, without limiting the invention to these examples.

Example 1

Organisms and Culture Conditions

*Tetrahymena thermophila* (Strains B1868 VII, B2086 II, B*VI, CU522 were provided by Dr. J. Gaertig, University of Georgia, Athens, Ga., USA) were grown in modified SPP medium (2% proteosepeptone, 0.1% yeast extract, 0.2% glucose, and 0.003% Fe-EDTA (Gaertig et al. (1994) PROC. NATL. ACAD. SCI. USA 91:4549–4553)); skim milk medium (2% skim milk powder, 0.5% yeast extract, 1% glucose, and 0.003% Fe-EDTA); or MYG medium (2% skim milk powder, 0.1% yeast extract, 0.2% glucose, and 0.003% Fe-EDTA) with the addition of an antibiotic solution (100 U/ml penicillin, 100 µg/ml streptomycin, and 0.25 µg/ml amphotericin B) (SPPA medium) at 30° C. in a 50 ml volume in a 250 ml Erlenmeyer flask, with shaking (150 rpm).

Plasmids and phages were reproduced and selected in *E. coli* XL1-Blue MRF', TOP10F', or JM109 cells. The bacteria were grown under standard conditions in LB or NZY medium with antibiotics in standard concentrations (Sambrook et al., 1989).

Example 2

Preparation of a *Tetrahymena Thermophila* cDNA Library

Total RNA was isolated from *Tetrahymena thermophila* according to the guanidine thiocyanate/phenol/chloroform method (Chomzynski & Sacchi (1987) ANAL. BIOCHEM. 161: 156–159). From total RNA, mRNA was extracted using Oligotex™ mRNA Purification System (Qiagen, Germany). The synthesis of cDNA was performed according to the Stratagene ZAP Express® cDNA Synthesis and Cloning Kit (Stratagene, LaJolla, Calif.). Following ligation of EcoRI adapters and digestion with Xho I, the cDNA was separated on an agarose gel according to size (S: 500–1500 bp, B: greater than 1500 bp). The cDNA was purified from the gel (QIAquick™ Gel Extraction Kit; Qiagen) and ligated into the ZAP express vector which had been cut with EcoRI and Xho I. The ligated cDNA was then packaged into phage in vitro (Gigapack® III Gold; Stratagene). The phage were reproduced in *E. coli* XL1-Blue MRF'. The S-cDNA library contained approximately 5×10$^5$ clones with an average insertion size of 1.1 kb, and the B-cDNA library contained approximately 6×10$^4$ clones with an average insertion size of 2 kb.

Example 3

Preparing a *Tetrahymena Thermophila* Genomic DNA Library

Genomic DNA was isolated from *Tetrahymena* by the Urea Method (Gaertig et al., 1994). The genomic DNA was digested with EcoRI and the cut DNA was then ligated into an EcoRI-digested Lambda vector (ZapExpress, Stratagene). The library was generated using a method similar to the method described for cDNA library preparation in Example 2.

Example 4

RT-PCR with Triterpenoid Cyclase-specific Primers

Sequence comparisons of known pentacyclic triterpenoid cyclases were used to identify conserved regions. PCR primers were designed for the highly conserved regions, GSWF/YGR/SWGV/I and DGGWGE, taking into consideration the ciliate codon or *Tetrahymena* codon usage (Wuitschick & Karrer (1999) J. EUKARYOT. MICROBIOL. 1999 46(3):239–47; CUTG, (Codon Usage Tabulated from gene library): http://www.dna.affrc.go.jp/~nakamura/CUTG.html).

The following primers were used for the PCR reactions:

SEQ ID No. 1:    5'-GGTTCNTGGTAYGGTAGATGGG-3';

and

SEQ ID No. 2:    5'-TTCACCCCAACCACCATC-3'.

Isolated mRNA (100 ng) was used for the initial strand synthesis catalyzed by the enzyme, AMV Reverse Transcriptase (Boehringer Mannheim, Indianapolis, Ind.). According to the manufacturer's protocol, the final reaction volume was 20 µl and contained: 50 mM Tris-HCl (pH 8.5), 8 mM MgCl$_2$, 30 mM KCl, 1 mM DTT, 1 mM dNTPs, 2 U AMV Reverse Transcriptase, and 2 pmol Oligo-dT anchor primer, SEQ ID No. 3: 5'-GACCACGCGTATCGATGTCG ACT$_{16}$V-3'.

The reaction was incubated for 1 hour at 55° C., followed by a 10-minute incubation at 65° C. An aliquot (¹/₁₀ volume) of the initial strand reaction was used for the PCR. The PCR reaction volume was 25 µl: 1% HotStarTaq™ PCR Buffer (Qiagen, Germany), 10 pmol of each gene-specific primer (SEQ ID No. 1 and SEQ ID No. 2), 200 µM dNTPs, 1.5 mM MgCl$_2$, and 1 U HotStarTaq™ DNA Polymerase (Qiagen). The PCR reaction was performed under the following conditions: an initial denaturization at 95° C. for 15 minutes, followed by 35 cycles at 94° C. for 30 seconds, 45° C. for 30 seconds, 72° C. for 1 minute, and a final incubation at 72° C. for 10 minutes. The PCR fragments were ligated into the TA Cloning® vector, pCR 2.1, using the TA Cloning® kit (Invitrogen, San Diego, Calif.), and then transformed into *E. coli* TOP10F' (Invitrogen). Plasmid DNA was isolated from positive clones (QIAprep® Spin kit, Qiagen) and sequenced.

Example 5

Isolation of the Triterpenoid Cyclase cDNA

Based on a preliminary sequence, new oligonucleotide primers were designed for PCR, SEQ ID No. 4: 5'-CTGT-TGGAGCTGTTGTACCAGG-3' and SEQ ID No. 5: 5'-CG-TAATTGACTCTTGCTAAACCTGG-3'.

The triterpenoid cyclase cDNA was generated by PCR using these primers in combination with vector-specific primers (T3 and T7). An aliquot of the S-cDNA library (2 µl; 10$^5$ PFU/µl) was used for the PCR reaction (see Example 2). PCR was performed according to the following protocol: DNA denaturization for 15 minutes at 95° C.; followed by 35 cycles at 94° C. for 20 seconds, 57° C. for 20 seconds, 72° C. for 2 minutes; and a final incubation at 72° C. for 10 minutes. The PCR products then were cloned (see Example 2) and sequenced.

A new primer was designed based on this sequence information. The primer was located at the 5'-end of the cDNA sequence, SEQ ID No. 6:5'-GCTAAAACTCTTTC ATACATGAAGAAG-3'.

Using this primer in combination with a vector-specific primer, the complete cDNA was amplified by PCR (see above for PCR conditions) from the cDNA library. The PCR product was sequenced and the corresponding cDNA sequence is listed as SEQ ID No. 11. The protein sequence can be derived from the cDNA sequence taking into consideration the specific codon usage.

Example 6

Isolation of the Genomic Sequence of Triterpenoid Cyclase

By screening a genomic library with a digoxigenin-labeled PCR-generated triterpenoid cyclase, a clone was isolated with a DNA insert of approximately 5000 bp. The clone was isolated from the phage by in vitro excision producing the plasmid pgTHC. The DNA insert was sequenced (SEQ ID No. 13) by primer walking. Comparing the cDNA sequence (SEQ ID No. 11) with this sequence, the introns and flanking sequences were identified (FIG. 4).

Example 7

Preparation of Triterpenoid Cyclase Knockout Constructs

A neo-cassette plasmid, p4T2-1ΔH3, (Gaertig et al., 1994) was inserted into the genomic sequence of *Tetrahymena* to produce the genetic knockout. The construct contains a neomycin resistance gene regulated by the *Tetrahymena* histone H4 promoter and the 3' flanked sequence of the BTU2 (β-tubulin 2) gene. In *Tetrahymena*, this plasmid provides resistance to paromomycin. The plasmid p4T2-1ΔH3 was digested with EcoRV and Sma I. The resulting 1.4 kb fragment was then ligated into the EcoRV-digested plasmid pgTHC producing the plasmid pgTHC::neo. With a successful transformation, the gene for the triterpenoid cyclase was replaced by this construct by homologous recombination, and as a result, the cells were resistant to paromomycin.

Example 8

Preparation of the Expression Construct, pBTHC

The vector pBICH3 (Gaertig et al., 1999) contains the coding sequence for the *Ichthyophthirius* I antigen (G1) preprotein flanked by the non-coding, regulatory sequences of the *Tetrahymena thermophila* BTU1 (β-tubulin 1) gene. A modified plasmid (pBICH3-Nsi) with a Nsi I restriction site at the start codon (provided by J. Gaertig, University of Georgia, Athens, Ga., USA) was used to generate the tetrahymanol cyclase expression construct, pBTHC. The restriction sites, Nsi I and BamHI, were added by PCR to the 5' and 3' ends, respectively, of the coding sequence for *Tetrahymena* tetrahymanol cyclase. Isolated plasmid containing the complete cDNA sequence for tetrahymanol cyclase (pTHC) was used as the template for PCR. The primers, SEQ ID No. 7:
5;-CTCTTTCATACATGCATAAGATACTCATAGGC-3' and

Figure 6:
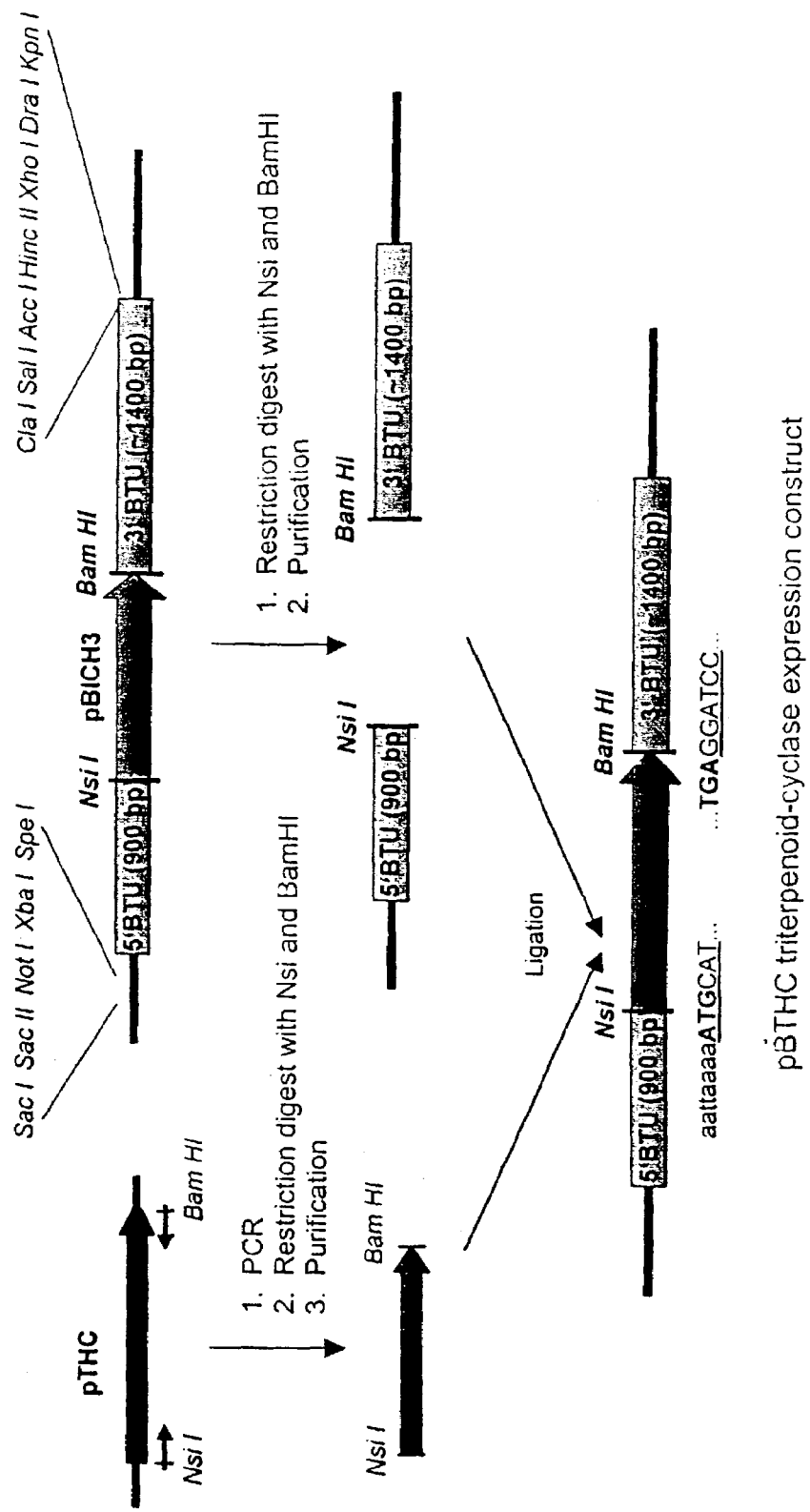
FIG. 6. Schematic diagram of the pBTHC triterpenoid expression construct. The plasmid (pBICH3-Nsi), which contains the non-coding, regulatory sequences of the *Tetrahymena thermophila* BTU1 (β-tubulin 1) gene with a Nsi I restriction site at the start codon, was used to generate the tetrahymanol cyclase expression construct, pBTHC. The restriction sites, Nsi I and BamHI, were added by PCR to the 5' and 3' ends, respectively, of the coding sequence for *Tetrahymena* tetrahymanol cyclase. The PCR-modified tetrahymanol cyclase and the plasmid pBICH3-Nsi were digested with the restriction enzymes, Nsi I and BamHI, and purified by an agarose gel. The digested tetrahymanol cyclase fragment was then ligated into the plasmid pBICH3-Nsi and the resulting expression vector, pBTHC, contained the complete coding sequence for triterpenoid cyclase in the correct reading frame and the regulatory sequences of the BTU1 gene.
Figure 7:
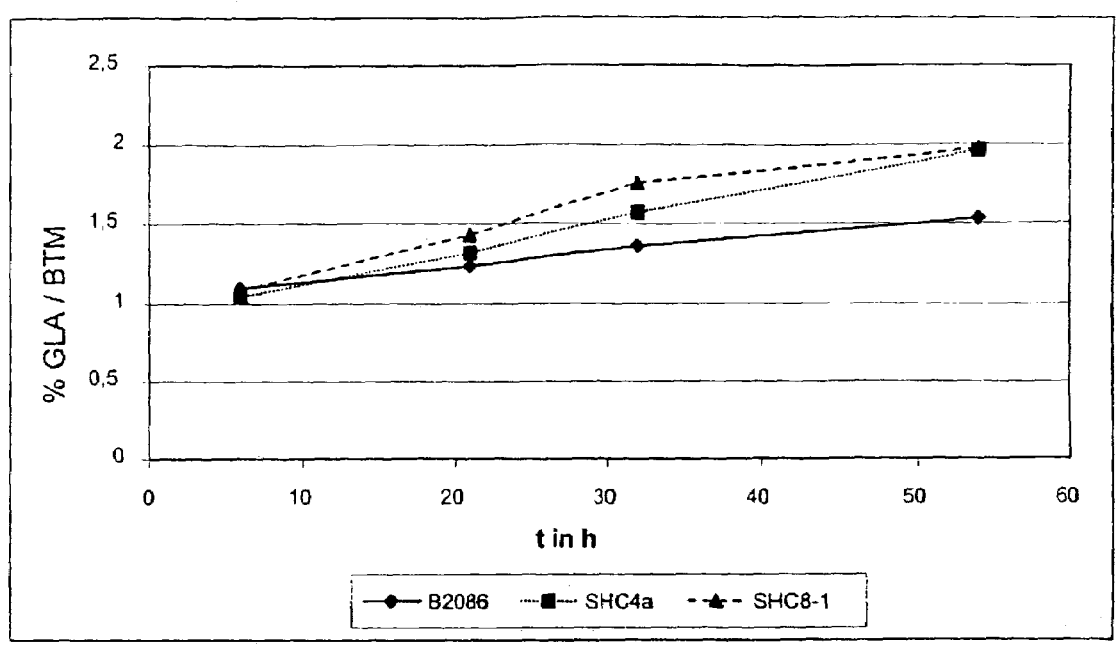
FIG. 7. Gamma-linolenic acid (GLA) in % of biodry mass of transformants compared with wild type *Tetrahymena*. The GLA content of the *Tetrahymena* triterpenoid cyclase knockout transformants was compared to *Tetrahymena* wild strain (B2086).
Figure 8:
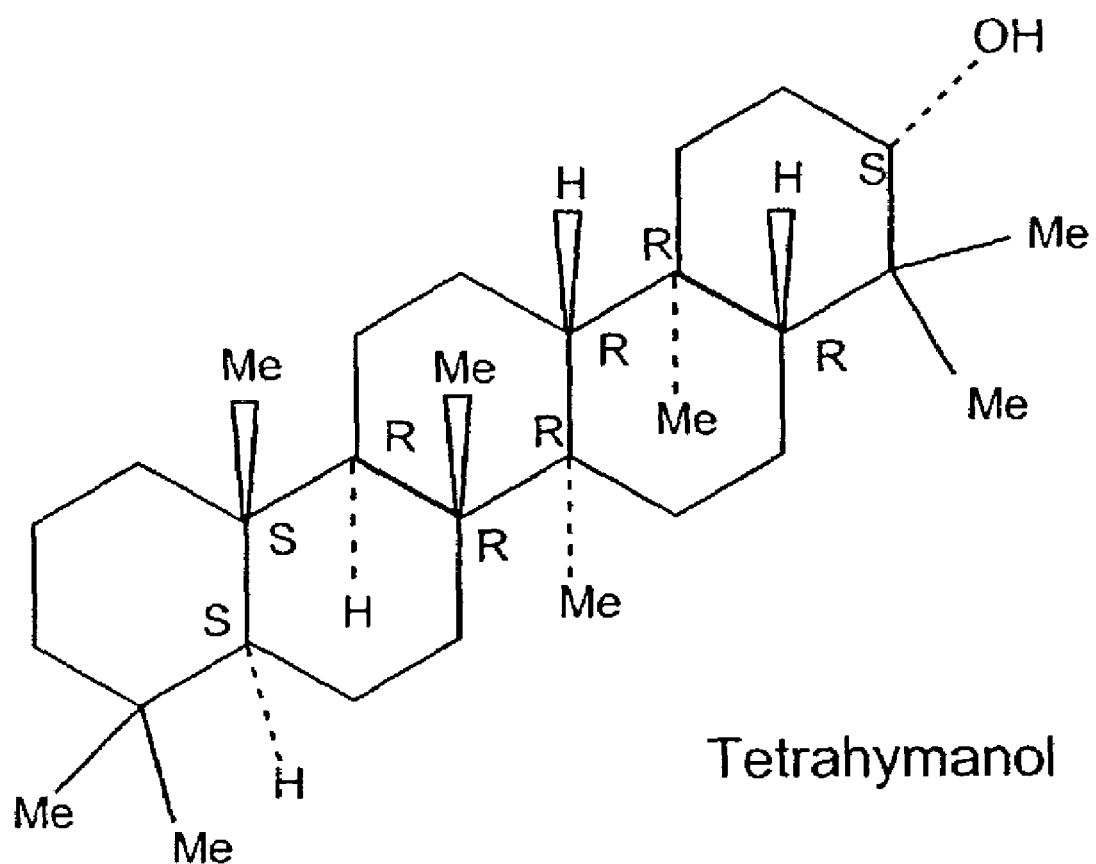
FIG. 8. Chemical structure of Tetrahymanol.

SEQ ID No. 8:
5'-GGCTTGGATCCTCAAATATTTTATTTTTATACAGG-3', were used to generate the PCR products, which contained the complete coding sequence of tetrahymanol cyclase flanked by Nsi I and BamHI restriction sites. The PCR products and the plasmid pBICH3-Nsi were digested with the restriction enzymes, Nsi I and BamHI, and purified by an agarose gel. The resulting expression vector, pBTHC, contained the complete coding sequence for triterpenoid cyclase in the correct reading frame and the regulatory sequences of the BTU1 gene (FIG. 6). For the transformation of *Tetrahymena*, the vectors were linearized by digestion with the restriction enzymes, Xba I and Sal I.

In a successful transformation, these constructs replaced the BTU1 gene via homologous recombination, and as a result, the cells were resistant to Paclitaxel.

Example 9

Determining the Fatty Acid Spectrum of the Transformants

The fatty acid spectrum was determined using a gas chromatography system with a flame ionization detector (HP GC 6890; Hewlett-Packard, Wilmington, Del.). An FFAP (Free Fatty Acid Phase) Permbond (Macherey & Nagel GmbH, Düren) was used as the column. The fatty acids were identified by comparing the retention times of fatty acid methyl ester standards. The concentration of fatty acids in the samples was determined on the basis of the known standard concentration. To determine the fatty acid spectrum, isolated transformants in MYG medium (plus 10 µg/ml cholesterol) were grown at 30° C. with shaking (150) rpm for 24–96 hours. An aliquot of the culture (50 ml) was centrifuged at 1500×g for 15 minutes. The supernatant was discarded and the pellet was frozen at −80° C. and subsequently freeze-dried. The lyophilized sample (50 mg) was resuspended in 1 ml of 20% methanolic HCl and 1 ml of methanolic standard solution (1 mg/ml). To release the fatty acids and their transesterification of fatty acid methyl ester, the samples were agitated in a water bath for two hours at 60° C., and then cooled to room temperature. Aqueous, saturated sodium hydrogen carbonate solution (1 ml) was added to neutralize the sample, and the samples were mixed carefully. The fatty acid methyl ester was extracted by the addition of n-Hexane. The sample was thoroughly mixed, and a phase separation was achieved by a 2-minute centrifugation at 4,300 rpm. About ⅔ of the upper, organic phase was removed, and 1 µl of the sample was injected into the GC column, and analyzed. The GLA content of the *Tetrahymena* triterpenoid cyclase knockout transformants as compared to the *Tetrahymena* wild strain (B2086) is shown in Table 1.

TABLE 1

| Time (hours) | % GLA/BTM B2086 | % GLA/BTM AX004a | % Difference AX004a | % GLA/BTM AX081 | % Difference AX081 |
|---|---|---|---|---|---|
| 6 | 1.10 | 1.03 | −6.8% | 1.08 | −1.9% |
| 21 | 1.24 | 1.32 | +6.5% | 1.44 | +16.1% |
| 32 | 1.37 | 1.57 | +14.6% | 1.76 | +28.5% |
| 54 | 1.54 | 1.96 | +27.3% | 1.98 | +28.6% |

GLA content of the *Tetrahymena* triterpenoid cyclase knockout transformants was compared to *Tetrahymena* wild strain (B2086). The table specifies the GLA percentile in the biodrymass (% GLA/BTM) and the percentile difference (% difference) of the transformants compared to the wild strain B2086.

Example 10

Macronucleus Transformation of *Tetrahymena* with the Tetrahymanol Cyclase Expression Construct, pBTHC

*Tetrahymena thermophila* cells ($5\times10^6$; CU522) were used for transformation. The cells were grown in 50 ml SPPA medium at 30° C. in a 250 ml Erlenmeyer flask on a shaker (150 rpm) to a cell density of approximately $3-5\times10^5$ cells/ml. The cells were pelleted for 5 minutes by centrifugation (1200×g). The cell pellets were resuspended in 50 ml of 10 mM Tris-HCl (pH 7.5), and then centrifuged as before. This washing step was repeated. The cells were resuspended in 10 mM Tris-HCl (pH 7.5) with antibiotics at a cell density of $3\times10^5$ cells/ml. The cells were transferred to a 250 ml Erlenmeyer flask, and incubated for 16–20 hours without shaking at 30° C. (starvation phase). Following the starvation phase, the number of cells was determined. The cells were centrifuged as above, and then resuspended in 10 mM Tris-HCl (pH 7.5) at a concentration of $5\times10^5$ cells/ml. One ml of cells was used for the transformation. The transformation was performed by microparticle bombardment (see Example 12). To regenerate, the cells were resuspended in SSPA medium, and incubated in an Erlenmeyer flask at 30° C. without shaking. After 3 hours, Paclitaxel was added to the medium in a final concentration of 20 µM. The cells were transferred in aliquots of 100 µl to 96-well microtiter plates and incubated in a humid, dark box at 30° C. After 2–3 days, the Paclitaxel-resistant clones were identified. Positive clones were hetero-inoculated in fresh medium with 25 µM Paclitaxel. By cultivating the cells with an increased Paclitaxel concentration (up to 80 µM), a complete "phenotypic assortment" was achieved as described by Gaertig & Kapler (1999).

To analyze the clones, DNA was extracted from approximately 4 ml cultures as described in Gaertig et al.(1994). DNA integrated in the BTU1 (β-tubulin 1) locus was amplified by PCR using BTU1-specific primers SEQ ID No. 9: 5'-AAAAATAAAAAAGTTTGAAAAAAAACCTTC-3', located approximately 50 bp upstream of the start codon; and SEQ ID No. 10: 5'-GTTTAGCTGACCGATTCAGT-TGTTC-3', 3 bp after the stop codon).

The PCR products was analyzed, uncut and cut with Hind III, Sac I or Pst I, on a 1% agarose gel. The complete "phenotypic assortment" was verified via RT-PCR with BTU1-specific primers (Gaertig & Kapler, 1999).

Example 11

Micronucleus and Macronucleus Transformation of *Tetrahymena* with the Knockout Construct, pgTHC::neo

*Tetrahymena* strains of varying pairing types (CU428 VII and B2086 II) were separated in SPPA medium at 30° C. with shaking (150 rpm), and cultivated in an Erlenmeyer flask. With a cell density of $3-5\times10^5$ cells/ml, the cell were washed three times with 50 ml of 10 mM Tris-HCl (pH 7.5), and then resuspended in 50 ml of 10 mM Tris-HCl (pH 7.5) diluted with an antibiotic solution. The cells were incubated in an Erlenmeyer flask at 30° C. without shaking. After approximately 4 hours, both cultures were recounted and diluted with 10 mM Tris-HCl (pH 7.5) to $3-5\times10^5$ cells and incubated for an additional 16–20 hours at 30° C. Following the starvation phase, the same (absolute) number of cells from each of the two cultures was mixed in a 2-liter Erlenmeyer flask. The cells were incubated at 30° C. (start of conjugation) and after 2 hours, the efficiency of the conjugation was determined. To ensure a successful transformation, approximately 30% of the cells should be in the form of pairs.

For the micronucleus transformation, at 3, 3.5, 4, and 4.5 hour timepoints following the start of conjugation, $1\times10^7$ conjugated cells ($5\times10^6$ pairs) were centrifuged for 5 minutes at 1200×g. The cell pellet was resuspended in 1 ml of 10 mM Tris-HCl (pH 7.5).

For transformation of the new macronucleus systems, 11 hours following the start of conjugation, the cells were centrifuged as above and suspended in the Tris-HCl. The transformation was performed by microparticle bombardment (see Example 12). Cholesterol (10 µg/ml) was added to the medium for cultivating the tetrahymanol cyclase knockout mutants.

The transformed cells were identified by paromomycin resistance selection. During the transformation of the micronucleus, paromomycin (100 µg/ml final concentration) was added 11 hours after the start of the conjugation. The cells were distributed in aliquots of 100 µl onto 96-well microtiter plates and then incubated in a moist box at 30° C. After 2–3 days, the paromomycin resistant clones were identified. Genuine micronucleus transformants could be differentiated by a comparison with the resistance for 6-methylpurin.

During the transformation of the macronucleus, paromomycin (100 µg/ml final concentration) was added approximately 4 hours following the transformation. The cells were distributed in aliquots of 100 µl onto 96-well microtiter plates and then incubated in a moist box at 30° C. After 2–3 days the resistant clones were identified. Positive clones were hetero-inoculated in fresh medium containing 120 µg/ml paromomycin. By culturing the cells in this high concentration of paromomycin, a complete "phenotypic assortment" (Gaertig & Kapler, 1999) was achieved.

By crossing micronucleus transformants with a B*VI strain, homozygous knockout mutants were generated (Bruns & Cassidy-Hanley (1999) METHODS IN CELL BIOLOGY 62:229–240).

Example 12

Biolistic Transformation (Microparticle Bombardment)

The transformation of *Tetrahymena thermophila* is achieved by the methods described by Bruns & Cassidy-Hanley (1999) METHODS IN CELL BIOLOGY 62:501–512; Gaertig et al. (1999); and Cassidy-Hanley et al.(1997) GENETICS 146:135–147. The use of the Biolistic® PDS-1000/He Particle Delivery System (BIO-RAD) is detailed in the manufacturer's manual.

For the transformation, gold particles (6 mg; 0.6 µm; BIO-RAD) were loaded with linearized plasmid DNA (10 µg) as described by Sanford et al. (1991) BIOTECHNIQUES 3:3–16; and Bruns & Cassidy-Hanley (1999).

Preparation of the gold particles. The gold particles were resuspended in 1 ml ethanol and then thoroughly vortexed 3 times for 1–2 minutes. Subsequently, the particles were centrifuged for 1 minute at 10,000×g, and the supernatant was carefully removed with a pipet. The gold particles were then resuspended in 1 ml sterile water and centrifuged as described above. This wash phase was repeated. The particles were then resuspended in 1 ml 50% glycerol and stored in aliquots of 100 μl at −20° C.

Loading the gold particles with DNA. All preparation was performed at 4° C. The gold particles, DNA vector, 2.5 M CaCl$_2$, 1 M spermidine, 70% and 100% ethanol were cooled on ice. The linearized DNA vector (10 μl; 1 μg/ml) was added to the gold particles (100 μl) and carefully vortexed for 10 seconds. Initially, 2.5 M CaCl$_2$ (100 μl) was added to the DNA-gold particles, vortexed for 10 seconds, and then spermidine (40 μl) was added and the sample was carefully vortexed for 10 minutes. Following the addition of 70% ethanol (200 μl), the DNA-gold particles were vortexed for 1 minute and then centrifuged for 1 minute at 10,000×g. The pellets were resuspended in 100% ethanol (20 μl), centrifuged, and then resuspended in 35 μl 100% ethanol.

Preparation of the macrocarrier. The macrocarrier holder, macrocarrier, and stop screens were placed in 100% ethanol for several hours, and the rupture disks were placed in isopropanol. Subsequently, one macrocarrier was inserted into the macrocarrier and air-dried. The prepared gold particles were then placed carefully in the center of the macrocarrier using a pipet. The macrocarrier was stored in a box with hygroscopic silica gel until the transformation.

Transformation. Prepared cells (1 ml) were placed in the center of a circular filter which was situated in a Petri dish. The filter was moistened with 10 mM Tris-HCl (pH 7.5), and placed into the lowest insert slot of the transformation chamber of the Biolistic® PDS-100/He Particle Delivery System. Transformation with the prepared gold particles was performed at a pressure of 900 psi (two 450 psi rapture disks) and a vacuum of 27 mmHg in the transformation chamber. The cells were then transferred immediately to an Erlenmeyer flask with 50 ml SPPA medium and incubated at 30° C., without shaking.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The disclosures of all references and publications cited above are expressly incorporated by reference in their entireties to the same extent as if each were incorporated by reference individually.

We claim:

1. A method of enriching the unsaturated fatty acid content in a host cell comprising the step of inactivating the transcription of a nucleic acid encoding a polypeptide comprising the amino acid sequence of SEQ ID NO: 12; in said host cell.

2. The method of claim 1, wherein said nucleic acid is inactivated by an antisense nucleic acid specific for said nucleic acid.

3. The method of claim 1, wherein said nucleic acid is inactivated by a method selected from the group consisting of deletion of said nucleic acid, insertion of a nucleic acid, and mutation of said nucleic acid.

4. The method of claim 3, wherein said nucleic acid is replaced with one or more selectable markers.

5. The method of claim 1, wherein the squalene content in the host cell in enriched.

* * * * *

SEQUENCE LISTING

```
<160> NUMBER OF SEQ ID NOS: 23

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: any nucleotide
<220> FEATURE:
<221> NAME/KEY: modified_base
<222> LOCATION: (12)
<223> OTHER INFORMATION: any pyrimidine

<400> SEQUENCE: 1
ggttcntggt anggtagatg gg                                              22

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 2
ttcaccccaa ccaccatc                                                   18

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Primer
```

```
<400> SEQUENCE: 3
gaccacgcgt atcgatgtcg acttttttttt tttttttttv                    39

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
ctgttggagc tgttgtacca gg                                         22

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
cgtaattgac tcttgctaaa cctgg                                      25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 6
gctaaaactc tttcatacat gaagaag                                    27

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 7
ctctttcata catgcataag atactcatag gc                              32

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 8
ggcttggatc ctcaaatatt ttatttttat acagg                           35

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
aaaaataaaa aagtttgaaa aaaaaccttc                                 30

<210> SEQ ID NO 10
<211> LENGTH: 22
```

```
<212> TYPE: DNA
<213> ORGANISM: Artificial Sequence
<220> FEATURE:
<223> OTHER INFORMATION: Description of Artificial Sequence: Primer

<400> SEQUENCE: 10
gtttagctga ccgattcagt tc                                              22

<210> SEQ ID NO 11
<211> LENGTH: 2072
<212> TYPE: DNA
<213> ORGANISM: Tetrahymena thermophila

<400> SEQUENCE: 11
aaaaaagcta aaactctttc atacatgaag aagatactca taggcttaat tataggtctc      60
tttttattct caagcgttaa tgccagcgtt aatctcactg aagtctaaaa tgccatctct     120
atctagcaag gcattaattg ggcagaagta cacaacaata cttggtacta tcctccttac     180
ttaggcgaaa tgtttatcag tgaatactac ttcgagttac tcgtcttgaa ttggactcat     240
aaatctgctt tcaacgctac atactttaca gaacgtctcc tctagactta attcgaagat     300
ggttcatggg agcaagtcag agaacaaaat cttgaaactg ttagttaga tgctactgtc      360 tttaactact ggtacttaaa gtctattaac aacaatccta aaattgaagc tgctctataa     420
aaggctagaa aatggatagt tgcttagggt ggtattgaag caactcaaac aatgaccaag     480
tttaagttag cagccttcgg ttaatacagt tgggaagatt tatggtatgt cccattgttc     540
atcttcaagt agaatggaat tttcaaatat acctacgtta aggatattgt tgcataatgg     600
gtctatccac atttaactgc cttagcttat ttgcgttact aaagaactgt tttcaatgtt     660
cctgttgctg atttgagaga gctctggatc aattacccta agaacggtat taaaatcagt     720
ccaagagaat actctacact taatcctgat agcgatctct tgatcttaat ggacgaaatc     780
ttcaaactta acaacctct ggaagtttc ggtgcctaca ctatttcaac cctcttgact       840
ttaatgtcct tcaaagactt ttagtcaaag caccctcatc tataccaaaa cgaaatacaa     900
aaggcttacg aagacggata ctatttcgtt gagtttaact actttaactt tagagaagct     960
tatcacggct ctttggatga tggtagatgg tgggatacca ttcttattag ttgggctatg    1020
cttgaaagtg gctaagataa agaaagaatc ttccctatcg tataaaatat ggtcaaagaa    1080
ggtctttaac ctaaaaaagg tataggttat ggatatgatt tcgaatatgc tcctgacact    1140
gatgacactg gattacttct cgttgttatg agttactaca aagaagcctt ctaaaagtaa    1200
atccctgaaa ctattgaatg gcttttctct atgcaaaatg acgatggtgg ctatccagct    1260
tttgacaaag gtaaaaatga agacaattta ttgttcaagt ttgccttcaa tatggctggt    1320
attgctaact cagctgaaat cttcgatccc tcatgtcctg atattactgg tcacatcatg    1380
gaaggattgg gtgagtttgg atatcaagct aatcatcctt agatttaaaa tatgattaaa    1440
tatcaaagaa agacttagaa caagtgggga tcttggtaag ctagatgggg tgtaaattac    1500
attatggctg ttggagctgt tgtaccaggt ttagcaagag tcaattacga cttaaatgaa    1560
cagtgggtac aaaatagtat aaattatttg cttaataaat aaaataaaga tggtggcttt    1620
ggtgaatgtg tcctttctta taatgatcct gaaaagtgga atggtatagg taaatctact    1680
gtcactcaaa cctcatgggg actattagct ctttagaag tttataatta aaatgaacaa     1740
attaagcatg ctgcagatag agctgcttag tatttattag attaattcaa agagacgat     1800 aataccttct atgatcactc cacaatagga acaggtcaca gaggattact ctatttatag    1860
```

```
taccccctcat atgcacaatc attcccatta gtagctttaa atagatacta aaaaatatct    1920
caaggttaat atcacttctc caaaaatttg tacaatggta atggagaacc tgtataaaaa    1980
taaaatattt gaaaattcaa taaactgtat tttacatttt aaatttattt gtattttttt    2040
aagttatttt ttcataaaat aaaaaaaaaa aa                                 2072
```

<210> SEQ ID NO 12
<211> LENGTH: 655
<212> TYPE: PRT
<213> ORGANISM: Tetrahymena thermophila

<400> SEQUENCE: 12

```
Met Lys Lys Ile Leu Ile Gly Leu Ile Ile Gly Leu Phe Leu Phe Ser
  1               5                  10                  15

Ser Val Asn Ala Ser Val Asn Leu Thr Glu Val Gln Asn Ala Ile Ser
             20                  25                  30

Ile Gln Gln Gly Ile Asn Trp Ala Glu Val His Asn Asn Thr Trp Tyr
         35                  40                  45

Tyr Pro Pro Tyr Leu Gly Glu Met Phe Ile Ser Glu Tyr Tyr Phe Glu
     50                  55                  60

Leu Leu Val Leu Asn Trp Thr His Lys Ser Ala Phe Asn Ala Thr Tyr
 65                  70                  75                  80

Phe Thr Glu Arg Leu Leu Gln Thr Gln Phe Glu Asp Gly Ser Trp Glu
                 85                  90                  95

Gln Val Arg Glu Gln Asn Leu Glu Thr Gly Gln Leu Asp Ala Thr Val
            100                 105                 110

Phe Asn Tyr Trp Tyr Leu Lys Ser Ile Asn Asn Asn Pro Lys Ile Glu
        115                 120                 125

Ala Ala Leu Gln Lys Ala Arg Lys Trp Ile Val Ala Gln Gly Gly Ile
    130                 135                 140

Glu Ala Thr Gln Thr Met Thr Lys Phe Lys Leu Ala Ala Phe Gly Gln
145                 150                 155                 160

Tyr Ser Trp Glu Asp Leu Trp Tyr Val Pro Leu Phe Ile Phe Lys Gln
                165                 170                 175

Asn Gly Ile Phe Lys Tyr Thr Tyr Val Lys Asp Ile Val Ala Gln Trp
            180                 185                 190

Val Tyr Pro His Leu Thr Ala Leu Ala Tyr Leu Arg Tyr Gln Arg Thr
        195                 200                 205

Val Phe Asn Val Pro Val Ala Asp Leu Arg Glu Leu Trp Ile Asn Tyr
    210                 215                 220

Pro Lys Asn Gly Ile Lys Ile Ser Pro Arg Glu Tyr Ser Thr Leu Asn
225                 230                 235                 240

Pro Asp Ser Asp Leu Leu Ile Leu Met Asp Glu Ile Phe Lys Leu Lys
                245                 250                 255

Gln Pro Leu Gly Ser Phe Gly Ala Tyr Thr Ile Ser Thr Leu Leu Thr
            260                 265                 270

Leu Met Ser Phe Lys Asp Phe Gln Ser Lys His Pro His Leu Tyr Gln
        275                 280                 285

Asn Glu Ile Gln Lys Ala Tyr Glu Asp Gly Tyr Tyr Phe Val Glu Phe
    290                 295                 300

Asn Tyr Phe Asn Phe Arg Glu Ala Tyr His Gly Ser Leu Asp Asp Gly
305                 310                 315                 320

Arg Trp Trp Asp Thr Ile Leu Ile Ser Trp Ala Met Leu Glu Ser Gly
                325                 330                 335
```

```
Gln Asp Lys Glu Arg Ile Phe Pro Ile Val Gln Asn Met Val Lys Glu
            340                 345                 350
Gly Leu Gln Pro Lys Lys Gly Ile Gly Tyr Gly Tyr Asp Phe Glu Tyr
            355                 360                 365
Ala Pro Asp Thr Asp Asp Thr Gly Leu Leu Val Val Met Ser Tyr
    370                 375                 380
Tyr Lys Glu Ala Phe Gln Lys Gln Ile Pro Glu Thr Ile Glu Trp Leu
385                 390                 395                 400
Phe Ser Met Gln Asn Asp Asp Gly Gly Tyr Pro Ala Phe Asp Lys Gly
                405                 410                 415
Lys Asn Glu Asp Asn Leu Leu Phe Lys Phe Ala Phe Asn Met Ala Gly
                420                 425                 430
Ile Ala Asn Ser Ala Glu Ile Phe Asp Pro Ser Cys Pro Asp Ile Thr
                435                 440                 445
Gly His Ile Met Glu Gly Leu Gly Glu Phe Gly Tyr Gln Ala Asn His
            450                 455                 460
Pro Gln Ile Gln Asn Met Ile Lys Tyr Gln Arg Lys Thr Gln Asn Lys
465                 470                 475                 480
Trp Gly Ser Trp Gln Ala Arg Trp Gly Val Asn Tyr Ile Met Ala Val
                485                 490                 495
Gly Ala Val Val Pro Gly Leu Ala Arg Val Asn Tyr Asp Leu Asn Glu
                500                 505                 510
Gln Trp Val Gln Asn Ser Ile Asn Tyr Leu Leu Asn Lys Gln Asn Lys
            515                 520                 525
Asp Gly Gly Phe Gly Glu Cys Val Leu Ser Tyr Asn Asp Pro Glu Lys
530                 535                 540
Trp Asn Gly Ile Gly Lys Ser Thr Val Thr Gln Thr Ser Trp Gly Leu
545                 550                 555                 560
Leu Ala Leu Leu Glu Val Tyr Asn Gln Asn Glu Gln Ile Lys His Ala
                565                 570                 575
Ala Asp Arg Ala Ala Gln Tyr Leu Leu Asp Gln Phe Lys Arg Asp Asp
                580                 585                 590
Asn Thr Phe Tyr Asp His Ser Thr Ile Gly Thr Gly His Arg Gly Leu
                595                 600                 605
Leu Tyr Leu Gln Tyr Pro Ser Tyr Ala Gln Ser Phe Pro Leu Val Ala
            610                 615                 620
Leu Asn Arg Tyr Gln Lys Ile Ser Gln Gly Gln Tyr His Phe Ser Lys
625                 630                 635                 640
Asn Leu Tyr Asn Gly Asn Gly Glu Pro Val Gln Lys Gln Asn Ile
                645                 650                 655

<210> SEQ ID NO 13
<211> LENGTH: 5046
<212> TYPE: DNA
<213> ORGANISM: Tetrahymena thermophila

<400> SEQUENCE: 13
gaattcatac attttttgata gttcagaaaa taattatttt aatttaattt tttaatcatt    60
ccctcataat ttaataataa ttaaaaatta agactgcata tattaaggca ctttactttt   120
ataaaattaa ttttctacat tataaatac agaagtattt tattatatat attttttcaaa   180 gtaaatgatt agcttttatt gattaaaatt aatgtgtgat taataatgtt acaatagcaa   240
tataagaaat attagtaaat cattataaga aaatataaac aagatagcat tcatatgcaa   300
aattaatttc tagaaatagt attcaaaaat gaagttaaaa tcctaagtac caactaatct   360
```

```
ttttaacata acctcattat tacgaaaata ttattatttt tttagtcact gtttgctaaa      420
tcgtatgatc ttttttataaa tctaaaaaaa caaagtaaaa tttaaatatg agtatggctt     480
gtttctaaat ctatttagtg aaagctaatt tcaatttata tgtatttaga gaagcattaa     540
gttaatagga gggggaaaa cgatgaaaaa ttaaaagtta ttgataagaa ttatttgtaa      600
tattatgttg taagttaaga attaataata ttattaaagg aatagaaagt tcttttaata    660
atattattaa agaaaaattg atatgtttga ggtgatgtca tgacgaaatt acatattatc    720
atgaacaaat caatggaaaa attgactgag ctaaaataaa aattgacgta aagagtttta    780
agtgcgtgtt agatttgaaa aagttaagaa aaatgacatg aatactggga ctttaataat    840
attatatatg taaggaattt attatattaa attcgtttca agttaaattc aaatttggct    900
taatattgtt agcaattaat tgattgtata gtcaacctta gctttaaaaa ccaactctaa    960
cttcaaggtt ttaataatat tattaatcaa ctcataaatt agtaaataag aaaaaagcta   1020
aaactctttc atacatgaag aagatactca taggcttaat tataggtctc tttttattct   1080
caagcgttaa tgccagcgtt aatctcactg aagtctaaaa tgccatctct atctagcaag   1140
gcattaattg ggcagaagta cacaacaata cttggtacta tcctccttac ttaggcgaaa   1200
tgtttatcag tgaatactac ttcgagttac tcgtcttgaa ttggactcat aaatctgctt   1260
tcaacgctac atactttaca gaacgtctcc tctagactta attcgaagat ggttcatggg   1320
agcaagtcag agaacaaaat cttgaaactg gttagttaga tgctactgtc tttaactact   1380
ggtacttaaa gtctattaac aacaatccta aaattgaagc tgctctataa aaggctagaa   1440
aatggatagt tgcttagggt ggtattgaag caactcaaac aatgaccaag tttaagttag   1500
cagccttcgg ttaatacagg taaagtttct ttttcatcaa tattttagaa ataaacaatc   1560 aatttttaaat tattctccca tattttgctc aaataataat ttctacttaa ataattagct   1620
tcaactgcaa atataaaaat gaattaattt attataaata aaagcagtaa atataagcaa   1680
atatactaat ttaattagct tattattctg ttaatattta aaagccattt tgactcaata   1740
gcttatttta ttttaaataa ttaaatagtt gggaagattt atggtatgtc ccattgttca   1800
tcttcaagta gaatggaatt ttcaaatata cctacgttaa ggatattgtt gcataatggg   1860
tctatccaca tttaactgcc ttagcttatt tgcgttacta aagaactgtt tcaatgttc    1920 ctgttgctga tttgagagag ctctggatca attaccctaa taacggtatt aaaatcagtc   1980
caagagaata ctctacactt aatcctgata gcgatctctt gatcttaatg gacgaaatct   2040
tcaaacttaa acaacctctt ggaagtttcg gtgcctacac tatttcaacc ctcttgactt   2100
taatgtcctt caaagacttt tagtcaaagc accctcatct ataccaaaac gaaatacaaa   2160
aggcttacga agacggatac tatttcgttg agtttaacta ctttaacttt agagaagctt   2220
atcacggctc tttggatgat ggtagatggt gggataccat tcttattagt tgggctatgc   2280
ttgaaagtgg ctaagataaa gaaagaatct tccctatcgt ataaaatatg gtcaaagaag   2340
gtctttaacc taaaaaaggt ataggttatg gatatgattt cgaatatgct cctgacactg   2400
atgacactgg attacttctc gttgttatga gttactacaa agaagccttc taaaagtaaa   2460
tccctgaaac tattgaatgg cttttctcta tgcaaaatga cgatggtggc tatccagctt   2520
ttgacaaagg taatttaata ttgataattt attccatttc tttatttaat aaaaataaat   2580
cttttaatta tttcaattga agatacatt taaataaaat tacaaatgta cttaaaataa    2640
atataatatt attaacactt ctactttatt ttaaaatagg taaaaatgaa gacaatttat   2700
```

```
tgttcaagtt tgccttcaat atggctggta ttgctaactc agctgaaatc ttcgatccct   2760
catgtcctga tattactggt cacatcatgg aaggattggg tgagtttgga tatcaagcta   2820
atcatcctta gatttaaaat atgattaaat atcaaagaaa gacttagaac aagtggggat   2880
cttggtaagc tagatggggt gtaaattaca ttatggctgt tggagctgtt gtaccaggtt   2940
tagcaagagt caattacgac ttaaatgaac agtgggtaca aaatagtata aattatttgc   3000
ttaataaata aaataaagat ggtggctttg gtgaatgtgt cctttcttat aatgatcctg   3060
aaaagtggaa tggtataggt aaatctactg tcactcaaac ctcatgggga ctattagctc   3120
ttttagaagt ttataattaa aatgaacaaa ttaagcatgc tgcagataga gctgcttagt   3180
atttattaga ttaattcaaa agagacgata ataccttcta tgatcactcc acaataggaa   3240
caggtcacag aggattactc tatttatagt acccctcata tgcacaatca ttcccattag   3300
tagctttaaa tagatactaa aaatatctc aaggttaata tcacttctcc aaaaatttgt   3360
acaatggtaa tggagaacct gtataaaaat aaaatatttg aaaattcaat aaactgtatt   3420
ttacatttta aatttatttg tattttttta agttattttt tcataaaata ataaataaat   3480
aaatttaatt tcatttttta tgaatttatt aatacacaaa aattttaatt attaattta   3540 aaaatcgcat ttattggttt atcaatattt taagtttaaa attattttca gcattttctt   3600
caatatcaaa attcatagtt ttgacatatt aaattattca atgagttttt tattttgct   3660 tttgtgagta atcaatcttt tttctaaatt tatattgcat taataaacaa atttaagtta   3720
tccattatca cttataatta tttagcatct aaaaattaat gcaaaacttt tttgatgaat   3780
cgattttact aagaattttt atttgttaaa ataagacaaa tgtaatttaa ataaattaat   3840
tccctcttaa attggtattt atttgtataa atctaattca tttaagtaga aattataatt   3900
aataattaaa ttagtaaaat gttatgatat taaacaaata aatagtatat gaatattata   3960
ttttaatcac atctcaatta gtatgctttt cgctgaataa aaagagcctt taataaatag   4020
tagtataatt tctttaaaat atacaatatt tttgaattaa ttggattta aataaataaa   4080 tatttattaa tttttaaaat ttttgatatt tttaatttaa aacttatttt ttctttcttt   4140
ctattatgct tattttgat attgaatagt agaagtgatt gatattaata attaaatatct   4200 tttttaaaat atcaaagtct taaaaaaat ataattaatt agttagttag ttacaaaata   4260
tggatagtta gcaacaaatc ggagatttat taactcatta cgaagctgag catttaatag   4320
aaaagttata aatcgttaac atagaagaat atggtagtta aatgtaaaat gctatttagt   4380 ttttagaca ttgttagtca tatcatcgca ctcacttaaa aattatcaat tatttataaa   4440
tagctggttc aagcaagacg aaattcttca aagactcaat atgcaagtat ttatttgcc   4500 attaatcaat tttattaaga aactatttca gcaaagatc taaattttat ttcaaaaact   4560
cattttacta atatatgcat taaagattta tcaaaaactt ttattattat tatacattta   4620
ttttagatta gaaaaaagaa ttaatatgaa gtaatgagtt ttgaagttat ttgctttact   4680
ttaacttaaa aataatttaa tattatgttt tttcaattaa catttttatca atcaaaatgc   4740 ttaagaaatt aaatttaaag atattttat atttcaaaaa tattttaggc acatgtcaat   4800
gcaatggtaa aaagtgatga gttcattatg gattctttag tgactttga taaagtgaag   4860 attttgattt acgatttaat agaaacagaa atttggaaat agaaggtatt gcctttacta   4920
aaaaatcaca tgcttaaaat aaacacatat agaagctata ttgctgtttta tcacgaagct   4980 gtagtctgta atttgctaga agtcattatg ttccatagaa ccgctgtcga ctcagctgat   5040
gaattc                                                               5046
```

<210> SEQ ID NO 14
<211> LENGTH: 563
<212> TYPE: PRT
<213> ORGANISM: Alicyclobacillus acidoterrestris

<400> SEQUENCE: 14

```
Ile Ile Ser Gln Arg Arg Glu Asp Gly Thr Trp Ser Ile Tyr Pro Gly
  1               5                  10                  15

Gly Pro Ser Asp Leu Asn Ala Thr Val Glu Ala Tyr Val Ala Leu Lys
             20                  25                  30

Tyr Leu Gly Glu Pro Ala Ser Asp Pro Gln Met Val Gln Ala Lys Glu
         35                  40                  45

Phe Ile Gln Asn Glu Gly Gly Ile Glu Ser Thr Arg Val Phe Thr Arg
 50                  55                  60

Leu Trp Leu Ala Met Val Gly Gln Tyr Pro Trp Asp Lys Leu Pro Val
 65                  70                  75                  80

Ile Pro Pro Glu Ile Met His Leu Pro Lys Ser Val Pro Leu Asn Ile
             85                  90                  95

Tyr Asp Phe Ala Ser Trp Ala Arg Ala Thr Ile Val Thr Leu Ser Tyr
            100                 105                 110

Arg His Glu Ser Pro Thr Cys Asp Ala Thr Ser Gly Leu Cys Lys Gly
        115                 120                 125

Ser Gly Ile Val Arg Gly Glu Gly Pro Pro Lys Arg Arg Ser Ala Lys
130                 135                 140

Gly Gly Asp Ser Gly Phe Phe Val Ala Leu Asp Lys Phe Leu Lys Ala
145                 150                 155                 160

Tyr Asn Lys Trp Pro Ile Gln Pro Gly Arg Lys Ser Gly Glu Gln Lys
                165                 170                 175

Ala Leu Glu Trp Ile Leu Ala His Gln Glu Ala Asp Gly Cys Trp Gly
            180                 185                 190

Gly Ile Gln Pro Pro Trp Phe Tyr Ala Leu Leu Ala Leu Lys Cys Leu
        195                 200                 205

Asn Met Thr Asp His Pro Ala Phe Val Lys Gly Phe Glu Gly Leu Glu
210                 215                 220

Ala Tyr Gly Val His Thr Ser Asp Gly Gly Trp Met Phe Gln Ala Ser
225                 230                 235                 240

Ile Ser Pro Ile Trp Asp Thr Gly Leu Thr Val Leu Ala Leu Arg Ser
                245                 250                 255

Ala Gly Leu Pro Pro Asp His Pro Ala Leu Ile Lys Ala Gly Glu Trp
            260                 265                 270

Leu Val Ser Lys Gln Ile Leu Lys Asp Gly Asp Trp Lys Val Arg Arg
        275                 280                 285

Arg Lys Ala Lys Pro Gly Gly Trp Ala Phe Glu Phe His Cys Glu Asn
290                 295                 300

Tyr Pro Asp Val Asp Asp Thr Ala Met Val Val Leu Ala Leu Asn Gly
305                 310                 315                 320

Ile Gln Leu Pro Asp Glu Gly Lys Arg Arg Asp Ala Leu Thr Arg Gly
                325                 330                 335

Phe Arg Trp Leu Arg Glu Met Gln Ser Ser Asn Gly Gly Trp Gly Ala
            340                 345                 350

Tyr Asp Val Asp Asn Thr Arg Gln Leu Thr Lys Ser Asp Ser Ile Phe
        355                 360                 365

Ala Thr Ser Gly Glu Val Ile Asp Pro Pro Ser Glu Asp Val Thr Ala
```

-continued

```
                   370                 375                 380

His Val Leu Glu Cys Phe Gly Ser Phe Gly Tyr Asp Glu Ala Trp Lys
385                 390                 395                 400

Val Ile Arg Lys Ala Val Glu Tyr Leu Lys Ala Gln Gln Arg Pro Asp
                405                 410                 415

Gly Ser Trp Phe Gly Arg Trp Gly Val Asn Tyr Val Tyr Gly Ile Gly
            420                 425                 430

Ala Val Val Pro Gly Leu Lys Ala Val Gly Val Asp Met Arg Glu Pro
                435                 440                 445

Trp Val Gln Lys Ser Leu Asp Trp Leu Val Glu His Gln Asn Glu Asp
450                 455                 460

Gly Gly Trp Gly Glu Asp Cys Arg Ser Tyr Asp Asp Pro Arg Leu Ala
465                 470                 475                 480

Gly Gln Gly Val Ser Thr Pro Ser Gln Thr Ala Trp Ala Leu Met Ala
                485                 490                 495

Leu Ile Ala Gly Gly Arg Val Glu Ser Asp Ala Val Leu Arg Gly Val
                500                 505                 510

Thr Tyr Leu His Asp Thr Gln Arg Ala Asp Gly Gly Trp Asp Glu Glu
            515                 520                 525

Val Tyr Thr Gly Thr Gly Phe Pro Gly Asp Phe Tyr Leu Ala Tyr Thr
        530                 535                 540

Met Tyr Arg Asp Ile Leu Pro Val Trp Ala Leu Gly Arg Tyr Gln Glu
545                 550                 555                 560

Ala Met Gln

<210> SEQ ID NO 15
<211> LENGTH: 559
<212> TYPE: PRT
<213> ORGANISM: Alicyclobacillus acidocaldarius

<400> SEQUENCE: 15

Leu Leu His Glu Gln Arg Glu Asp Gly Thr Trp Ala Leu Tyr Pro Gly
  1               5                  10                  15

Gly Pro Pro Asp Leu Asp Thr Thr Ile Glu Ala Tyr Val Ala Leu Lys
                20                  25                  30

Tyr Ile Gly Met Ser Arg Asp Glu Pro Met Gln Lys Ala Leu Arg
            35                  40                  45

Phe Ile Gln Ser Gln Gly Gly Ile Glu Ser Ser Arg Val Phe Thr Arg
        50                  55                  60

Met Trp Leu Ala Leu Val Gly Glu Tyr Pro Trp Glu Lys Val Pro Met
 65                  70                  75                  80

Val Pro Pro Glu Ile Met Phe Leu Gly Lys Arg Met Pro Leu Asn Ile
                85                  90                  95

Tyr Glu Phe Gly Ser Trp Ala Arg Ala Thr Val Val Ala Leu Ser Ile
            100                 105                 110

Val Met Ser Arg Gln Pro Val Phe Pro Leu Glu Arg Ala Arg Val
        115                 120                 125

Pro Glu Leu Tyr Glu Thr Asp Val Pro Pro Arg Arg Gly Ala Lys
130                 135                 140

Gly Gly Gly Gly Trp Ile Phe Asp Ala Leu Asp Arg Ala Leu His Gly
145                 150                 155                 160

Tyr Gln Lys Leu Ser Val His Pro Phe Arg Arg Ala Ala Glu Ile Arg
                165                 170                 175

Ala Leu Asp Trp Leu Leu Glu Arg Gln Ala Gly Asp Gly Ser Trp Gly
```

```
                         180                 185                 190
Gly Ile Gln Pro Pro Trp Phe Tyr Ala Leu Ile Ala Leu Lys Ile Leu
            195                 200                 205

Asp Met Thr Gln His Pro Ala Phe Ile Lys Gly Trp Glu Gly Leu Glu
210                 215                 220

Leu Tyr Gly Val Glu Leu Asp Tyr Gly Gly Trp Met Phe Gln Ala Ser
225                 230                 235                 240

Ile Ser Pro Val Trp Asp Thr Gly Leu Ala Val Leu Ala Leu Arg Ala
                245                 250                 255

Ala Gly Leu Pro Ala Asp His Asp Arg Leu Val Lys Ala Gly Glu Trp
            260                 265                 270

Leu Leu Asp Arg Gln Ile Thr Val Pro Gly Asp Trp Ala Val Lys Arg
        275                 280                 285

Pro Asn Leu Lys Pro Gly Gly Phe Ala Phe Gln Phe Asp Asn Val Tyr
    290                 295                 300

Tyr Pro Asp Val Asp Asp Thr Ala Val Val Val Trp Ala Leu Asn Thr
305                 310                 315                 320

Leu Arg Leu Pro Asp Glu Arg Arg Arg Asp Ala Met Thr Lys Gly
                325                 330                 335

Phe Arg Trp Ile Val Gly Met Gln Ser Ser Asn Gly Gly Trp Gly Ala
            340                 345                 350

Tyr Asp Val Asp Asn Thr Ser Asp Leu Pro Asn His Ile Pro Phe Cys
        355                 360                 365

Asp Phe Gly Glu Val Thr Asp Pro Pro Ser Glu Asp Val Thr Ala His
    370                 375                 380

Val Leu Glu Cys Phe Gly Ser Phe Gly Tyr Asp Asp Ala Trp Lys Val
385                 390                 395                 400

Ile Arg Arg Ala Val Glu Tyr Leu Lys Arg Glu Gln Lys Pro Asp Gly
                405                 410                 415

Ser Trp Phe Gly Arg Trp Gly Val Asn Tyr Leu Tyr Gly Thr Gly Ala
            420                 425                 430

Val Val Ser Ala Leu Lys Ala Val Gly Ile Asp Thr Arg Glu Pro Tyr
        435                 440                 445

Ile Gln Lys Ala Leu Asp Trp Val Glu Gln His Gln Asn Pro Asp Gly
    450                 455                 460

Gly Trp Gly Glu Asp Cys Arg Ser Tyr Glu Asp Pro Ala Tyr Ala Gly
465                 470                 475                 480

Lys Gly Ala Ser Thr Pro Ser Gln Thr Ala Trp Ala Leu Met Ala Leu
                485                 490                 495

Ile Ala Gly Gly Arg Ala Glu Ser Glu Ala Ala Arg Arg Gly Val Gln
            500                 505                 510

Tyr Leu Val Glu Thr Gln Arg Pro Asp Gly Gly Trp Asp Glu Pro Tyr
        515                 520                 525

Tyr Thr Gly Thr Gly Phe Pro Gly Asp Phe Tyr Leu Gly Tyr Thr Met
    530                 535                 540

Tyr Arg His Val Phe Pro Thr Leu Ala Leu Gly Arg Tyr Lys Gln
545                 550                 555

<210> SEQ ID NO 16
<211> LENGTH: 630
<212> TYPE: PRT
<213> ORGANISM: Alicyclobacillus acidocaldarius

<400> SEQUENCE: 16
```

-continued

```
Ala Glu Gln Leu Val Glu Ala Pro Ala Tyr Ala Arg Thr Leu Asp Arg
  1               5                  10                  15

Ala Val Glu Tyr Leu Leu Ser Cys Gln Lys Asp Glu Gly Tyr Trp Trp
             20                  25                  30

Gly Pro Leu Leu Ser Asn Val Thr Met Glu Ala Glu Tyr Val Leu Leu
             35                  40                  45

Cys His Ile Leu Asp Arg Val Asp Arg Asp Arg Met Glu Lys Ile Arg
         50                  55                  60

Arg Tyr Leu Leu His Glu Gln Arg Glu Asp Gly Thr Trp Ala Leu Tyr
 65              70                  75                  80

Pro Gly Gly Pro Pro Asp Leu Asp Thr Thr Ile Glu Ala Tyr Val Ala
                 85                  90                  95

Leu Lys Tyr Ile Gly Met Ser Arg Asp Glu Pro Met Gln Lys Ala
             100                 105                 110

Leu Arg Phe Ile Gln Ser Gln Gly Gly Ile Glu Ser Ser Arg Val Phe
             115                 120                 125

Thr Arg Met Trp Leu Ala Leu Val Gly Glu Tyr Pro Trp Glu Lys Val
             130                 135                 140

Pro Met Val Pro Pro Glu Ile Met Phe Leu Gly Lys Arg Met Pro Leu
145                 150                 155                 160

Asn Ile Tyr Glu Phe Gly Ser Trp Ala Arg Ala Thr Val Val Ala Leu
             165                 170                 175

Ser Ile Val Met Ser Arg Gln Pro Val Phe Pro Leu Pro Glu Arg Ala
             180                 185                 190

Arg Val Pro Glu Leu Tyr Glu Thr Asp Val Pro Pro Arg Arg Arg Gly
             195                 200                 205

Ala Lys Gly Gly Gly Trp Ile Phe Asp Ala Leu Asp Arg Ala Leu
210                 215                 220

His Gly Tyr Gln Lys Leu Ser Val His Pro Phe Arg Arg Ala Ala Glu
225                 230                 235                 240

Ile Arg Ala Leu Asp Trp Leu Leu Glu Arg Gln Ala Gly Asp Gly Ser
             245                 250                 255

Trp Gly Gly Ile Gln Pro Pro Trp Phe Tyr Ala Leu Ile Ala Leu Lys
             260                 265                 270

Ile Leu Asp Met Thr Gln His Pro Ala Phe Ile Lys Gly Trp Glu Gly
             275                 280                 285

Leu Glu Leu Tyr Gly Val Glu Leu Asp Tyr Gly Gly Trp Met Phe Gln
             290                 295                 300

Ala Ser Ile Ser Pro Val Trp Asp Thr Gly Leu Ala Val Leu Ala Leu
305                 310                 315                 320

Arg Ala Ala Gly Leu Pro Ala Asp His Asp Arg Leu Val Lys Ala Gly
                 325                 330                 335

Glu Trp Leu Leu Asp Arg Gln Ile Thr Val Pro Gly Asp Trp Ala Val
             340                 345                 350

Lys Arg Pro Asn Leu Lys Pro Gly Gly Phe Ala Phe Gln Phe Asp Asn
             355                 360                 365

Val Tyr Tyr Pro Asp Val Asp Asp Thr Ala Val Val Trp Ala Leu
             370                 375                 380

Asn Thr Leu Arg Leu Pro Asp Glu Arg Arg Arg Asp Ala Met Thr
385                 390                 395                 400

Lys Gly Phe Arg Trp Ile Val Gly Met Gln Ser Ser Asn Gly Gly Trp
             405                 410                 415

Gly Ala Tyr Asp Val Asp Asn Thr Ser Asp Leu Pro Asn His Ile Pro
```

-continued

```
            420                 425                 430
Phe Cys Asp Phe Gly Glu Val Thr Asp Pro Pro Ser Glu Asp Val Thr
        435                 440                 445

Ala His Val Leu Glu Cys Phe Gly Ser Phe Gly Tyr Asp Asp Ala Trp
450                 455                 460

Lys Val Ile Arg Arg Ala Val Glu Tyr Leu Lys Arg Glu Gln Lys Pro
465                 470                 475                 480

Asp Gly Ser Trp Phe Gly Arg Trp Gly Val Asn Tyr Leu Tyr Gly Thr
                485                 490                 495

Gly Ala Val Val Ser Ala Leu Lys Ala Val Gly Ile Asp Thr Arg Glu
                500                 505                 510

Pro Tyr Ile Gln Lys Ala Leu Asp Trp Val Glu Gln His Gln Asn Pro
            515                 520                 525

Asp Gly Gly Trp Gly Glu Asp Cys Arg Ser Tyr Glu Asp Pro Ala Tyr
        530                 535                 540

Ala Gly Lys Gly Ala Ser Thr Pro Ser Gln Thr Ala Trp Ala Leu Met
545                 550                 555                 560

Ala Leu Ile Ala Gly Gly Arg Ala Glu Ser Glu Ala Ala Arg Arg Gly
                565                 570                 575

Val Gln Tyr Leu Val Glu Thr Gln Arg Pro Asp Gly Gly Trp Asp Glu
                580                 585                 590

Pro Tyr Tyr Thr Gly Thr Gly Phe Pro Gly Asp Phe Tyr Leu Gly Tyr
            595                 600                 605

Thr Met Tyr Arg His Val Phe Pro Thr Leu Ala Leu Gly Arg Tyr Lys
        610                 615                 620

Gln Ala Ile Glu Arg Arg
625                 630

<210> SEQ ID NO 17
<211> LENGTH: 634
<212> TYPE: PRT
<213> ORGANISM: Alicyclobacillus acidocaldarius

<400> SEQUENCE: 17

Met Thr Lys Gln Leu Leu Asp Thr Pro Met Val Gln Ala Thr Leu Glu
1               5                   10                  15

Ala Gly Val Ala His Leu Leu Arg Arg Gln Ala Pro Asp Gly Tyr Trp
                20                  25                  30

Trp Ala Pro Leu Leu Ser Asn Val Cys Met Glu Ala Glu Tyr Val Leu
            35                  40                  45

Leu Cys His Cys Leu Gly Lys Lys Asn Pro Glu Arg Glu Ala Gln Ile
        50                  55                  60

Arg Lys Tyr Ile Ile Ser Gln Arg Arg Glu Asp Gly Thr Trp Ser Ile
65                  70                  75                  80

Tyr Pro Gly Gly Pro Ser Asp Leu Asn Ala Thr Val Glu Ala Tyr Val
                85                  90                  95

Ala Leu Lys Tyr Leu Gly Glu Pro Ala Ser Asp Pro Gln Met Val Gln
                100                 105                 110

Ala Lys Glu Phe Ile Gln Asn Glu Gly Gly Ile Glu Ser Thr Arg Val
            115                 120                 125

Phe Thr Arg Leu Trp Leu Ala Met Val Gly Gln Tyr Pro Trp Asp Lys
        130                 135                 140

Leu Pro Val Ile Pro Pro Glu Ile Met His Leu Pro Lys Ser Val Pro
145                 150                 155                 160
```

-continued

```
Leu Asn Ile Tyr Asp Phe Ala Ser Trp Ala Arg Ala Thr Ile Val Thr
            165                 170                 175

Leu Ser Tyr Arg His Glu Ser Pro Thr Cys Asp Ala Thr Ser Gly Leu
            180                 185                 190

Cys Lys Gly Ser Gly Ile Val Arg Gly Glu Gly Pro Pro Lys Arg Arg
            195                 200                 205

Ser Ala Lys Gly Gly Asp Ser Gly Phe Phe Val Ala Leu Asp Lys Phe
210                 215                 220

Leu Lys Ala Tyr Asn Lys Trp Pro Ile Gln Pro Gly Arg Lys Ser Gly
225                 230                 235                 240

Glu Gln Lys Ala Leu Glu Trp Ile Leu Ala His Gln Glu Ala Asp Gly
                245                 250                 255

Cys Trp Gly Gly Ile Gln Pro Pro Trp Phe Tyr Ala Leu Leu Ala Leu
            260                 265                 270

Lys Cys Leu Asn Met Thr Asp His Pro Ala Phe Val Lys Gly Phe Glu
            275                 280                 285

Gly Leu Glu Ala Tyr Gly Val His Thr Ser Asp Gly Gly Trp Met Phe
            290                 295                 300

Gln Ala Ser Ile Ser Pro Ile Trp Asp Thr Gly Leu Thr Val Leu Ala
305                 310                 315                 320

Leu Arg Ser Ala Gly Leu Pro Pro Asp His Pro Ala Leu Ile Lys Ala
                325                 330                 335

Gly Glu Trp Leu Val Ser Lys Gln Ile Leu Lys Asp Gly Asp Trp Lys
            340                 345                 350

Val Arg Arg Lys Ala Lys Pro Gly Gly Trp Ala Phe Glu Phe His
            355                 360                 365

Cys Glu Asn Tyr Pro Asp Val Asp Asp Thr Ala Met Val Val Leu Ala
            370                 375                 380

Leu Asn Gly Ile Gln Leu Pro Asp Glu Gly Lys Arg Arg Asp Ala Leu
385                 390                 395                 400

Thr Arg Gly Phe Arg Trp Leu Arg Glu Met Gln Ser Ser Asn Gly Gly
                405                 410                 415

Trp Gly Ala Tyr Asp Val Asp Asn Thr Arg Gln Leu Thr Lys Ser Asp
            420                 425                 430

Ser Ile Phe Ala Thr Ser Gly Glu Val Ile Asp Pro Pro Ser Glu Asp
            435                 440                 445

Val Thr Ala His Val Leu Glu Cys Phe Gly Ser Phe Gly Tyr Asp Glu
450                 455                 460

Ala Trp Lys Val Ile Arg Lys Ala Val Glu Tyr Leu Lys Ala Gln Gln
465                 470                 475                 480

Arg Pro Asp Gly Ser Trp Phe Gly Arg Trp Gly Val Asn Tyr Val Tyr
                485                 490                 495

Gly Ile Gly Ala Val Pro Gly Leu Lys Ala Val Gly Val Asp Met
            500                 505                 510

Arg Glu Pro Trp Val Gln Lys Ser Leu Asp Trp Leu Val Glu His Gln
            515                 520                 525

Asn Glu Asp Gly Gly Trp Gly Glu Asp Cys Arg Ser Tyr Asp Asp Pro
            530                 535                 540

Arg Leu Ala Gly Gln Gly Val Ser Thr Pro Ser Gln Thr Ala Trp Ala
545                 550                 555                 560

Leu Met Ala Leu Ile Ala Gly Gly Arg Val Glu Ser Asp Ala Val Leu
                565                 570                 575

Arg Gly Val Thr Tyr Leu His Asp Thr Gln Arg Ala Asp Gly Gly Trp
```

```
                          580                 585                 590
Asp Glu Glu Val Tyr Thr Gly Thr Gly Phe Pro Gly Asp Phe Tyr Leu
            595                 600                 605

Ala Tyr Thr Met Tyr Arg Asp Ile Leu Pro Val Trp Ala Leu Gly Arg
            610                 615                 620

Tyr Gln Glu Ala Met Gln Arg Ile Arg Gly
625                 630

<210> SEQ ID NO 18
<211> LENGTH: 647
<212> TYPE: PRT
<213> ORGANISM: Synechocystis sp.

<400> SEQUENCE: 18

Met Val Ile Ala Ala Ser Pro Ser Val Pro Cys Pro Ser Thr Glu Gln
  1               5                  10                  15

Val Arg Gln Ala Ile Ala Ala Ser Arg Asp Phe Leu Leu Ser Glu Gln
             20                  25                  30

Tyr Ala Asp Gly Tyr Trp Trp Ser Glu Leu Glu Ser Asn Val Thr Ile
         35                  40                  45

Thr Ala Glu Val Val Ile Leu His Lys Ile Trp Gly Thr Ala Ala Gln
     50                  55                  60

Arg Pro Leu Glu Lys Ala Lys Asn Tyr Leu Leu Gln Gln Gln Arg Asp
 65                  70                  75                  80

His Gly Gly Trp Glu Leu Tyr Tyr Gly Asp Gly Gly Glu Leu Ser Thr
                 85                  90                  95

Ser Val Glu Ala Tyr Thr Ala Leu Arg Ile Leu Gly Val Pro Ala Thr
            100                 105                 110

Asp Pro Ala Leu Val Lys Ala Lys Asn Phe Ile Val Gly Arg Gly Gly
        115                 120                 125

Ile Ser Lys Ser Arg Ile Phe Thr Lys Met His Leu Ala Leu Ile Gly
    130                 135                 140

Cys Tyr Asp Trp Arg Gly Thr Pro Ser Ile Pro Pro Trp Val Met Leu
145                 150                 155                 160

Leu Pro Asn Asn Phe Phe Asn Ile Tyr Glu Met Ser Ser Trp Ala
                165                 170                 175

Arg Ser Ser Thr Val Pro Leu Met Ile Val Cys Asp Gln Lys Pro Val
            180                 185                 190

Tyr Asp Ile Ala Gln Gly Leu Arg Val Asp Glu Leu Tyr Ala Glu Gly
        195                 200                 205

Met Glu Asn Val Gln Tyr Lys Leu Pro Glu Ser Gly Thr Ile Trp Asp
    210                 215                 220

Ile Phe Ile Gly Leu Asp Ser Leu Phe Lys Leu Gln Glu Gln Ala Lys
225                 230                 235                 240

Val Val Pro Phe Arg Glu Gln Gly Leu Ala Leu Ala Glu Lys Trp Ile
                245                 250                 255

Leu Glu Arg Gln Glu Val Ser Gly Asp Trp Gly Gly Ile Ile Pro Ala
            260                 265                 270

Met Leu Asn Ser Leu Leu Ala Leu Lys Val Leu Gly Tyr Asp Val Asn
        275                 280                 285

Asp Leu Tyr Val Gln Arg Gly Leu Ala Ala Ile Asp Asn Phe Ala Val
    290                 295                 300

Glu Thr Glu Asp Ser Tyr Ala Ile Gln Ala Cys Val Ser Pro Val Trp
305                 310                 315                 320
```

-continued

Asp Thr Ala Trp Val Arg Ala Leu Ala Glu Ala Asp Leu Gly Lys
            325                 330                 335

Asp His Pro Ala Leu Val Lys Ala Gly Gln Trp Leu Leu Asp Lys Gln
            340                 345                 350

Ile Leu Thr Tyr Gly Asp Trp Gln Ile Lys Asn Pro His Gly Glu Pro
            355                 360                 365

Gly Ala Trp Ala Phe Glu Phe Asp Asn Asn Phe Tyr Pro Asp Ile Asp
            370                 375                 380

Asp Thr Cys Val Val Met Met Ala Leu Gln Gly Ile Thr Leu Pro Asp
385                 390                 395                 400

Glu Glu Arg Lys Gln Gly Ala Ile Asn Lys Ala Leu Gln Trp Ile Ala
                405                 410                 415

Thr Met Gln Cys Lys Thr Gly Gly Trp Ala Ala Phe Asp Ile Asp Asn
            420                 425                 430

Asp Gln Asp Trp Leu Asn Gln Leu Pro Tyr Gly Asp Leu Lys Ala Met
            435                 440                 445

Ile Asp Pro Ser Thr Ala Asp Ile Thr Ala Arg Val Val Glu Met Leu
450                 455                 460

Gly Ala Cys Gly Leu Thr Met Asp Ser Pro Arg Val Glu Arg Gly Leu
465                 470                 475                 480

Thr Tyr Leu Leu Gln Glu Gln Glu Gln Asp Gly Ser Trp Phe Gly Arg
                485                 490                 495

Trp Gly Val Asn Tyr Leu Tyr Gly Thr Ser Gly Ala Leu Ser Ala Leu
                500                 505                 510

Ala Ile Tyr Asp Ala Gln Arg Phe Ala Pro Gln Ile Lys Thr Ala Ile
            515                 520                 525

Ala Trp Leu Leu Ser Cys Gln Asn Ala Asp Gly Gly Trp Gly Glu Thr
            530                 535                 540

Cys Glu Ser Tyr Lys Asn Lys Gln Leu Lys Gly Gln Gly Asn Ser Thr
545                 550                 555                 560

Ala Ser Gln Thr Ala Trp Ala Leu Ile Gly Leu Leu Asp Ala Leu Lys
            565                 570                 575

Tyr Leu Pro Ser Leu Gly Gln Asp Ala Lys Leu Thr Thr Ala Ile Glu
            580                 585                 590

Gly Gly Val Ala Phe Leu Val Gln Gly Gln Thr Pro Lys Gly Thr Trp
            595                 600                 605

Glu Glu Ala Glu Tyr Thr Gly Thr Gly Phe Pro Cys His Phe Tyr Ile
            610                 615                 620

Arg Tyr His Tyr Tyr Arg Gln Tyr Phe Pro Leu Ile Ala Leu Ala Arg
625                 630                 635                 640

Tyr Ser His Leu Gln Ala Ser
            645

<210> SEQ ID NO 19
<211> LENGTH: 680
<212> TYPE: PRT
<213> ORGANISM: Streptomyces coelicolor

<400> SEQUENCE: 19

Met Thr Ala Thr Thr Asp Gly Ser Thr Gly Ala Ser Leu Arg Pro Leu
1               5                   10                  15

Ala Ala Ser Ala Ser Asp Thr Asp Ile Thr Ile Pro Ala Ala Ala Ala
                20                  25                  30

Gly Val Pro Glu Ala Ala Ala Arg Ala Thr Arg Arg Ala Thr Asp Phe
            35                  40                  45

```
Leu Leu Ala Lys Gln Asp Ala Glu Gly Trp Trp Lys Gly Asp Leu Glu
     50                  55                  60

Thr Asn Val Thr Met Asp Ala Glu Asp Leu Leu Arg Gln Phe Leu
 65                  70                  75                  80

Gly Ile Gln Asp Glu Glu Thr Thr Arg Ala Ala Leu Phe Ile Arg
                 85                  90                  95

Gly Glu Gln Arg Glu Asp Gly Thr Trp Ala Thr Phe Tyr Gly Gly Pro
                100                 105                 110

Gly Glu Leu Ser Thr Thr Ile Glu Ala Tyr Val Ala Leu Arg Leu Ala
                115                 120                 125

Gly Asp Ser Pro Glu Ala Pro His Met Ala Arg Ala Ala Glu Trp Ile
    130                 135                 140

Arg Ser Arg Gly Gly Ile Ala Ser Ala Arg Val Phe Thr Arg Ile Trp
145                 150                 155                 160

Leu Ala Leu Phe Gly Trp Trp Lys Trp Asp Asp Leu Pro Glu Leu Pro
                165                 170                 175

Pro Glu Leu Ile Tyr Phe Pro Thr Trp Val Pro Leu Asn Ile Tyr Asp
                180                 185                 190

Phe Gly Cys Trp Ala Arg Gln Thr Ile Val Pro Leu Thr Ile Val Ser
        195                 200                 205

Ala Lys Arg Pro Val Arg Pro Ala Pro Phe Pro Leu Asp Glu Leu His
    210                 215                 220

Thr Asp Pro Ala Arg Pro Asn Pro Pro Arg Pro Leu Ala Pro Val Ala
225                 230                 235                 240

Ser Trp Asp Gly Ala Phe Gln Arg Ile Asp Lys Ala Leu His Ala Tyr
                245                 250                 255

Arg Lys Val Ala Pro Arg Arg Leu Arg Arg Ala Ala Met Asn Ser Ala
                260                 265                 270

Ala Arg Trp Ile Ile Glu Arg Gln Glu Asn Asp Gly Cys Trp Gly Gly
        275                 280                 285

Ile Gln Pro Pro Ala Val Tyr Ser Val Ile Ala Leu Tyr Leu Leu Gly
    290                 295                 300

Tyr Asp Leu Glu His Pro Val Met Arg Ala Gly Leu Glu Ser Leu Asp
305                 310                 315                 320

Arg Phe Ala Val Trp Arg Glu Asp Gly Ala Arg Met Ile Glu Ala Cys
                325                 330                 335

Gln Ser Pro Val Trp Asp Thr Cys Leu Ala Thr Ile Ala Leu Ala Asp
                340                 345                 350

Ala Gly Val Pro Glu Asp His Pro Gln Leu Val Lys Ala Ser Asp Trp
        355                 360                 365

Met Leu Gly Glu Gln Ile Val Arg Pro Gly Asp Trp Ser Val Lys Arg
    370                 375                 380

Pro Gly Leu Pro Pro Gly Gly Trp Ala Phe Glu Phe His Asn Asp Asn
385                 390                 395                 400

Tyr Pro Asp Ile Asp Asp Thr Ala Glu Val Val Leu Ala Leu Arg Arg
                405                 410                 415

Val Arg His His Asp Pro Glu Arg Val Glu Lys Ala Ile Gly Arg Gly
                420                 425                 430

Val Arg Trp Asn Leu Gly Met Gln Ser Lys Asn Gly Ala Trp Gly Ala
        435                 440                 445

Phe Asp Val Asp Asn Thr Ser Ala Phe Pro Asn Arg Leu Pro Phe Cys
450                 455                 460
```

```
Asp Phe Gly Glu Val Ile Asp Pro Pro Ser Ala Asp Val Thr Ala His
465                 470                 475                 480

Val Val Glu Met Leu Ala Val Glu Gly Leu Ala His Asp Pro Arg Thr
                485                 490                 495

Arg Arg Gly Ile Gln Trp Leu Leu Asp Ala Gln Glu Thr Asp Gly Ser
            500                 505                 510

Trp Phe Gly Arg Trp Gly Val Asn Tyr Val Tyr Gly Thr Gly Ser Val
        515                 520                 525

Ile Pro Ala Leu Thr Ala Ala Gly Leu Pro Thr Ser His Pro Ala Ile
    530                 535                 540

Arg Arg Ala Val Arg Trp Leu Glu Ser Val Gln Asn Glu Asp Gly Gly
545                 550                 555                 560

Trp Gly Glu Asp Leu Arg Ser Tyr Arg Tyr Val Arg Glu Trp Ser Gly
                565                 570                 575

Arg Gly Ala Ser Thr Ala Ser Gln Thr Gly Trp Ala Leu Met Ala Leu
            580                 585                 590

Leu Ala Ala Gly Glu Arg Asp Ser Lys Ala Val Glu Arg Gly Val Ala
        595                 600                 605

Trp Leu Ala Ala Thr Gln Arg Glu Asp Gly Ser Trp Asp Glu Pro Tyr
    610                 615                 620

Phe Thr Gly Thr Gly Phe Pro Trp Asp Phe Ser Ile Asn Tyr Asn Leu
625                 630                 635                 640

Tyr Arg Gln Val Phe Pro Leu Thr Ala Leu Gly Arg Tyr Val His Gly
                645                 650                 655

Glu Pro Phe Ala Lys Lys Pro Arg Ala Ala Asp Ala Pro Ala Glu Ala
            660                 665                 670

Ala Pro Ala Glu Val Lys Gly Ser
        675                 680

<210> SEQ ID NO 20
<211> LENGTH: 757
<212> TYPE: PRT
<213> ORGANISM: Arabidopsis thaliana

<400> SEQUENCE: 20

Met Trp Lys Leu Lys Ile Gly Lys Gly Asn Gly Glu Asp Pro His Leu
1               5                   10                  15

Phe Ser Ser Asn Asn Phe Val Gly Arg Gln Thr Trp Lys Phe Asp His
                20                  25                  30

Lys Ala Gly Ser Pro Glu Glu Arg Ala Val Glu Glu Ala Arg Arg
            35                  40                  45

Gly Phe Leu Asp Asn Arg Phe Arg Val Lys Gly Cys Ser Asp Leu Leu
    50                  55                  60

Trp Arg Met Gln Phe Leu Arg Glu Lys Lys Phe Glu Gln Gly Ile Pro
65                  70                  75                  80

Gln Leu Lys Ala Thr Asn Ile Glu Glu Ile Thr Tyr Glu Thr Thr Thr
                85                  90                  95

Asn Ala Leu Arg Arg Gly Val Arg Tyr Phe Thr Ala Leu Gln Ala Ser
            100                 105                 110

Asp Gly His Trp Pro Gly Glu Ile Thr Gly Pro Leu Phe Phe Leu Pro
        115                 120                 125

Pro Leu Ile Phe Cys Leu Tyr Ile Thr Gly His Leu Glu Glu Val Phe
    130                 135                 140

Asp Ala Glu His Arg Lys Glu Met Leu Arg His Ile Tyr Cys His Gln
145                 150                 155                 160
```

-continued

```
Asn Glu Asp Gly Gly Trp Gly Leu His Ile Glu Ser Lys Ser Val Met
            165                 170                 175
Phe Cys Thr Val Leu Asn Tyr Ile Cys Leu Arg Met Leu Gly Glu Asn
        180                 185                 190
Pro Glu Gln Asp Ala Cys Lys Arg Ala Arg Gln Trp Ile Leu Asp Arg
    195                 200                 205
Gly Gly Val Ile Phe Ile Pro Ser Trp Gly Lys Phe Trp Leu Ser Ile
210                 215                 220
Leu Gly Val Tyr Asp Trp Ser Gly Thr Asn Pro Thr Pro Glu Leu
225                 230                 235                 240
Leu Met Leu Pro Ser Phe Leu Pro Ile His Pro Gly Lys Ile Leu Cys
                245                 250                 255
Tyr Ser Arg Met Val Ser Ile Pro Met Ser Tyr Leu Tyr Gly Lys Arg
            260                 265                 270
Phe Val Gly Pro Ile Thr Pro Leu Ile Leu Leu Arg Glu Glu Leu
        275                 280                 285
Tyr Leu Glu Pro Tyr Glu Glu Ile Asn Trp Lys Lys Ser Arg Arg Leu
    290                 295                 300
Tyr Ala Lys Glu Asp Met Tyr Tyr Ala His Pro Leu Val Gln Asp Leu
305                 310                 315                 320
Leu Ser Asp Thr Leu Gln Asn Phe Val Glu Pro Leu Leu Thr Arg Trp
                325                 330                 335
Pro Leu Asn Lys Leu Val Arg Glu Lys Ala Leu Gln Leu Thr Met Lys
            340                 345                 350
His Ile His Tyr Glu Asp Glu Asn Ser His Tyr Ile Thr Ile Gly Cys
        355                 360                 365
Val Glu Lys Val Leu Cys Met Leu Ala Cys Trp Val Glu Asn Pro Asn
    370                 375                 380
Gly Asp Tyr Phe Lys Lys His Leu Ala Arg Ile Pro Asp Tyr Met Trp
385                 390                 395                 400
Val Ala Glu Asp Gly Met Lys Met Gln Ser Phe Gly Cys Gln Leu Trp
                405                 410                 415
Asp Thr Gly Phe Ala Ile Gln Ala Leu Leu Ala Ser Asn Leu Pro Asp
            420                 425                 430
Glu Thr Asp Asp Ala Leu Lys Arg Gly His Asn Tyr Ile Lys Ala Ser
        435                 440                 445
Gln Val Arg Glu Asn Pro Ser Gly Asp Phe Arg Ser Met Tyr Arg His
    450                 455                 460
Ile Ser Lys Gly Ala Trp Thr Phe Ser Asp Arg Asp His Gly Trp Gln
465                 470                 475                 480
Val Ser Asp Cys Thr Ala Glu Ala Leu Lys Cys Cys Leu Leu Leu Ser
                485                 490                 495
Met Met Ser Ala Asp Ile Gly Gly Gln Lys Ile Asp Asp Glu Gln Leu
            500                 505                 510
Tyr Asp Ser Val Asn Leu Leu Leu Ser Leu Gln Ser Gly Asn Gly Gly
        515                 520                 525
Val Asn Ala Trp Glu Pro Ser Arg Ala Tyr Lys Trp Leu Glu Leu Leu
    530                 535                 540
Asn Pro Thr Glu Phe Met Ala Asn Thr Met Val Glu Arg Glu Phe Val
545                 550                 555                 560
Glu Cys Thr Ser Ser Val Ile Gln Ala Leu Asp Leu Phe Arg Lys Leu
                565                 570                 575
```

```
Tyr Pro Asp His Arg Lys Lys Glu Ile Asn Arg Ser Ile Glu Lys Ala
            580                 585                 590
Val Gln Phe Ile Gln Asp Asn Gln Thr Pro Asp Gly Ser Trp Tyr Gly
            595                 600                 605
Asn Trp Gly Val Cys Phe Ile Tyr Ala Thr Trp Phe Ala Leu Gly Gly
            610                 615                 620
Leu Ala Ala Ala Gly Glu Thr Tyr Asn Asp Cys Leu Ala Met Arg Asn
625                 630                 635                 640
Gly Val His Phe Leu Leu Thr Thr Gln Arg Asp Asp Gly Gly Trp Gly
                645                 650                 655
Glu Ser Tyr Leu Ser Cys Ser Glu Gln Arg Tyr Ile Pro Ser Glu Gly
            660                 665                 670
Glu Arg Ser Asn Leu Val Gln Thr Ser Trp Ala Met Met Ala Leu Ile
            675                 680                 685
His Thr Gly Gln Ala Glu Arg Asp Leu Thr Pro Leu His Arg Ala Ala
    690                 695                 700
Lys Leu Ile Ile Asn Ser Gln Leu Glu Asn Gly Asp Phe Pro Gln Gln
705                 710                 715                 720
Glu Ile Val Gly Ala Phe Met Asn Thr Cys Met Leu His Tyr Ala Thr
                725                 730                 735
Tyr Arg Asn Thr Phe Pro Leu Trp Ala Leu Ala Glu Tyr Arg Lys Val
            740                 745                 750
Val Phe Ile Val Asn
        755
```

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: QW-motif
<220> FEATURE:
<221> NAME/KEY: MOD_RES
<222> LOCATION: (1)
<223> OTHER INFORMATION: K or R
<220> FEATURE:
<221> NAME/KEY: MOD_RES
<222> LOCATION: (2)..(4)
<223> OTHER INFORMATION: variable amino acid spanning 2-3 residues
<220> FEATURE:
<221> NAME/KEY: MOD_RES
<222> LOCATION: (5)
<223> OTHER INFORMATION: F, Y or W
<220> FEATURE:
<221> NAME/KEY: MOD_RES
<222> LOCATION: (7)..(9)
<223> OTHER INFORMATION: variable amino acid
<220> FEATURE:
<221> NAME/KEY: MOD_RES
<222> LOCATION: (11)..(15)
<223> OTHER INFORMATION: variable amino acid spanning 2-5 residues
<220> FEATURE:
<221> NAME/KEY: MOD_RES
<222> LOCATION: (17)
<223> OTHER INFORMATION: variable amino acid

<400> SEQUENCE: 21

```
Xaa Xaa Xaa Xaa Xaa Leu Xaa Xaa Xaa Gln Xaa Xaa Xaa Xaa Xaa Gly
  1               5                  10                  15
Xaa Trp
```

<210> SEQ ID NO 22
<211> LENGTH: 6
<212> TYPE: PRT

```
-continued

<213> ORGANISM: Artificial Sequence
<220> FEATURE:
<223> OTHER INFORMATION: Description of Artificial Sequence: conserved
      motif
<220> FEATURE:
<221> NAME/KEY: MOD_RES
<222> LOCATION: (2)
<223> OTHER INFORMATION: V or L

<400> SEQUENCE: 22

Asp Xaa Asp Asp Thr Ala
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: conserved
      motif

<400> SEQUENCE: 23

Asp Thr Asp Asp Thr Gly
 1               5
```